United States Patent
Inoue et al.

(10) Patent No.: US 10,350,192 B2
(45) Date of Patent: Jul. 16, 2019

(54) LACTATE DEHYDROGENASE INHIBITOR AND ANTIEPILEPTIC DRUG CONTAINING THE SAME

(71) Applicant: NATIONAL UNIVERSITY CORPORATION OKAYAMA UNIVERSITY, Okayama-shi, Okayama (JP)

(72) Inventors: Tsuyoshi Inoue, Okayama (JP); Nagisa Sada, Okayama (JP)

(73) Assignee: NATIONAL UNIVERSITY CORPORATION OKAYAMA UNIVERSITY, Okayama-shi (JP)

( * ) Notice: Subject to any disclaimer, the term of this patent is extended or adjusted under 35 U.S.C. 154(b) by 0 days.

(21) Appl. No.: 15/549,288

(22) PCT Filed: Feb. 9, 2016

(86) PCT No.: PCT/JP2016/053764
§ 371 (c)(1),
(2) Date: Aug. 7, 2017

(87) PCT Pub. No.: WO2016/129583
PCT Pub. Date: Aug. 18, 2016

(65) Prior Publication Data
US 2018/0015068 A1 Jan. 18, 2018

(30) Foreign Application Priority Data
Feb. 9, 2015 (JP) ................. 2015-023572

(51) Int. Cl.
| | | |
|---|---|---|
| C07D 317/48 | (2006.01) |
| C07D 317/60 | (2006.01) |
| A61K 31/36 | (2006.01) |
| A61K 31/4725 | (2006.01) |
| A61K 31/4741 | (2006.01) |
| A61K 31/496 | (2006.01) |
| C07D 405/04 | (2006.01) |
| C07D 405/06 | (2006.01) |
| C07D 407/04 | (2006.01) |
| C07D 407/06 | (2006.01) |
| C07D 413/04 | (2006.01) |
| C07D 417/06 | (2006.01) |
| C07D 405/14 | (2006.01) |
| C07D 317/50 | (2006.01) |
| C07D 317/54 | (2006.01) |
| C07D 453/02 | (2006.01) |
| C07D 487/08 | (2006.01) |
| C07D 491/06 | (2006.01) |
| C07D 495/04 | (2006.01) |

(52) U.S. Cl.
CPC .......... *A61K 31/36* (2013.01); *A61K 31/4725* (2013.01); *A61K 31/4741* (2013.01); *A61K 31/496* (2013.01); *C07D 317/50* (2013.01); *C07D 317/54* (2013.01); *C07D 317/60* (2013.01); *C07D 405/04* (2013.01); *C07D 405/06* (2013.01); *C07D 405/14* (2013.01); *C07D 407/04* (2013.01); *C07D 407/06* (2013.01); *C07D 413/04* (2013.01); *C07D 417/06* (2013.01); *C07D 453/02* (2013.01); *C07D 487/08* (2013.01); *C07D 491/06* (2013.01); *C07D 495/04* (2013.01)

(58) Field of Classification Search
CPC ..... A61K 31/36; C07D 317/48; C07D 317/60
See application file for complete search history.

(56) References Cited

U.S. PATENT DOCUMENTS

| | | |
|---|---|---|
| 3,910,959 A | 10/1975 | Vallet |
| 4,209,517 A | 6/1980 | Riveron et al. |
| 2009/0163545 A1 | 6/2009 | Goldfarb |

(Continued)

FOREIGN PATENT DOCUMENTS

| | | | |
|---|---|---|---|
| DE | 102005024012 A1 | 11/2006 |
| EP | 1640007 A1 | 3/2006 |

(Continued)

OTHER PUBLICATIONS

Robinson. Bioorganic and Medicinal Chemistry, 2005, 13, 4007-4013. (Year: 2005).*

(Continued)

*Primary Examiner* — Noble E Jarrell
(74) *Attorney, Agent, or Firm* — Westerman, Hattori, Daniels & Adrian, LLP

(57) ABSTRACT

The invention provides a lactate dehydrogenase inhibitor that makes it possible to suppress refractory epilepsy in which conventional antiepileptic drugs are ineffective, and an antiepileptic drug containing said inhibitor. The lactate dehydrogenase inhibitor of the invention contains a compound represented by formula (III); i.e., isosafrole or a compound having isosafrole as a scaffold, and the antiepileptic drug of the invention has these compounds as an active ingredient.

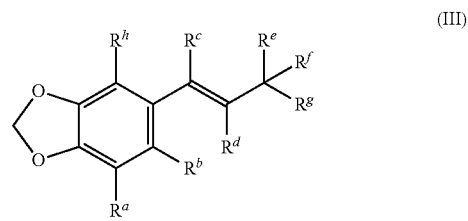

(III)

3 Claims, 17 Drawing Sheets

(56) References Cited

U.S. PATENT DOCUMENTS

| | | |
|---|---|---|
| 2012/0309794 A1 | 12/2012 | Minutolo et al. |
| 2013/0079336 A1 | 3/2013 | Mott et al. |

FOREIGN PATENT DOCUMENTS

| | | |
|---|---|---|
| JP | 2013-510106 A | 3/2013 |
| WO | 99/12540 A1 | 3/1999 |
| WO | 2014/115764 A1 | 7/2014 |

OTHER PUBLICATIONS

MISRA. Journal of the Indian Chemical Society, 1977, 54(6), 651-2 (Year: 1977).*

Lie et al., "Inhibition of endothelin A receptor protects brain microvascular endothelial cells against hypoxia-induced injury", International Journal of Molecular Medicine, 2014, vol. 34, No. 1, p. 313-320.

Baxendale et al., "Identification of compounds with anti-convulsant properties in a zebrafish model of epileptic seizures", Disease Models & Mechanisms, 2012, vol. 5, No. 6, p. 773-784.

Aukunuru et al., "Synthesis of Novel Piperonal Derivatives and Evaluation of their Anticonvulsant Activity using a Nanoparticular Formulation", International Journal of Pharmaceutical Sciences and Nanotechnology, Apr.-Jun. 2009, vol. 2, No. 1, p. 435-442.

Wang et al., "Chemical Structure-Physiological Activity Relationship in Cinnamamides and their Analogs. III., Relationship Between Chemical Structure and Anticonvulsant Action", Beijing Yixueyuan Xuebao, 1982, vol. 14, No. 1,. p. 65-70. With Partial English translation.

Zhang et al., "Relation between chemical structure and physiological activity in cinnamamides and their analogs. I. Study on anticonvulsant activity", Beijing Yixueyuan Xuebao, vol. 12, No. 2, 1980, p. 83-91. With English abstract.

Sada et al., "Targeting LDH enzymes with a stiripentol analog to treat epilepsy", Science, Mar. 20, 2015, vol. 437, p. 1362-1367.

Sirven et al., "Antiepileptic Drugs 2012: Recent Advances and Trends", Mayo Clinic Proceedings, Sep. 2012, vol. 87, No. 9, pp. 879-889.

Meldrum et al., "Molecular Targets for Antiepileptic Drug Development", Neurotherapeutics: The Journal of the American Society for Experimental NeuroTherapeutics, vol. 4, Jan. 2007, pp. 18-61.

Neal et al., "The ketogenic diet for the treatment of childhood epilepsy:a randomised controlled trial", Lancet Neurol, vol. 7, Jun. 2008, pp. 500-506.

Ma et al., "Ketogenic Diet Metabolites Reduce Firing in Central Neurons by Opening KATP Channels", The Journal of Neuroscience, Apr. 4, 2007, vol. 27, No. 14, pp. 3618-3625.

Juge et al., "Metabolic Control of Vesicular Glutamate Transport and Release", Neuron, vol. 68, Oct. 7, 2010, pp. 99-112.

Masino et al., "A ketogenic diet suppresses seizures in mice through adenosine A1 receptors", The Journal of Clinical Investigation, vol. 121, No. 7, Jul. 2011, pp. 2679-2683.

Perez et al., "Stiripentol: Efficacy and Tolerability in Children with Epilepsy", Epilepsia, vol. 40, No. 11, 1999, pp. 1618-1626.

Chiron et al., "Stiripentol in severe myoclonic epilepsy in infancy: a randomised placebo-controlled syndrome-dedicated trial", The Lancet, Nov. 11, 2000, vol. 356, pp. 1638-1642.

Chiron, "Stiripentol", Neurotherapeutics: The Journal of the American Society for Experimental NeuroTherapeutics, vol. 4, Jan. 2007, pp. 123-125.

Deck et al., "Selective Inhibitors of Human Lactate Dehydrogenases and Lactate Dehydrogenase from the Malarial Parasite *Plasmodium falciparum*", Journal of Medicinal Chemistry, vol. 41, 1998, pp. 3879-3887.

Cameron et al., "Identification and Activity of a Series of Azole-based Compounds with Lactate Dehydrogenase-directed Antimalarial Activity", The Journal of Biological Chemistry, vol. 279, No. 30, 2004, pp. 31429-31439.

Granchi et al., "Discovery of N-Hydroxyindole-Based Inhibitors of Human Lactate Dehydrogenase Isoform A (LDH-A) as Starvation Agents against Cancer Cells", Journal of Medicinal Chemistry, vol. 54, 2011, pp. 1599-1612.

Farabegoli et al., "Galloflavin, a new lactate dehydrogenase inhibitor, induces the death of human breast cancer cells with different glycolytic attitude by affecting distinct signaling pathways", European Journal of Pharmaceutical Sciences, Vo. 47, 2012, pp. 729-738.

Aboul-Enein et al., "Design and synthesis of novel stiripentol analogues as potential anticonvulsants", European Journal of Medicinal Chemistry, vol. 47, 2012, pp. 360-369.

Riban et al., "Evolution of Hippocampal Epileptic Activity Druing the Development of Hippocampal Sclerosis in a Mouse Model of Temporal Lobe Epilepsy", Neuroscience, vol. 112, No. 1, 2002, pp. 101-111.

Houser, "Granule cell dispersion in the dentate gyms of humans with temporal lobe epilepsy", Brain Research, vol. 535, 1990, pp. 195-204.

Shen et al., "Efficacy of stiripentol in the intravenous pentylenetetrazol infusion seizure model in the rat", Epilepsy Research, vol. 7, 1990, pp. 40-48.

Search Report dated May 17, 2016, issued in counterpart International Application No. PCT/JP2016/053764 (2 pages).

Husain, A. et al., "Synthesis and Biological Evaluation of 2-Arylidene-4-(4-methoxy-phenyl)but-3-en-4-olides", Asian Journal of Chemistry, Chemic Publishing, Sahibadad, IN, Jul. 1, 2005, vol. 17, No. 3, pp. 1579-1584; cited in Extended (supplementary) European Search Report dated Jul. 20, 2018.

Abramovitch, R.A. et al., "Internuclear Cyclisation. Part VIII. Naphth[3:2:1-cd]oxindoles", Journal of the Chemical Society, Jan. 1, 1954, pp. 1697-1703; cited in Extended (supplementary) European Search Report dated Jul. 20, 2018.

Li, J.T. et al, "Synthesis of 1,5-Diaryl-3-arylethenyl-2-pyrazolines Under Ultrasound Irradiation", Asian Journal of Chemistry, Chemic Publishing, Jan. 1, 2010, vol. 22, No. 1, pp. 589-592; cited in Extended (supplementary) European Search Report dated Jul. 20, 2018.

Robinson, T.P. et al., "Synthesis and biological evaluation of aromatic enones related to curcumin", Bioorganic & Medicinal Chemistry, Jun. 2, 2005, vol. 13, No. 12, pp. 4007-4013; cited in Extended (supplementary) European Search Report dated Jul. 20, 2018.

Salem, M.A.I. et al., "Study on 3,5-pyrazolidinedione and its derivatives. Part I", 1992, Database CA [Online] Chemical Abstracts Services, Columbus, Ohio, US; cited in Extended (supplementary) European Search Report dated Jul. 20, 2018. (2 pages).

Tang. J. et al., "Kavalactones Yangonin and Methysticin Induce Apoptosis in Human Hepatocytes (HepG2) In Vitro" Phytotherapy Research, Jan. 1, 2011, pp. 417-423; cited in Extended (supplementary) European Search Report dated Jul. 20, 2018.

Extended (supplementary) European Search Report dated Jul. 20, 2018, issued in counterpart European Application No. 16749227.1. (19 pages).

* cited by examiner

FIG. 6-2

| Compound No. | R¹ | R² |
|---|---|---|
| 10 | H | -C(CH₃)₂-OH |
| 11 | H | 4-(OCHF₂)-phenyl |
| 12 | Br | 2-pyridyl |
| 13 | H | 2-pyrrolyl |

| Compound No.14 | (E)-1-(benzo[d][1,3]dioxol-5-yl)-3-phenylprop-2-en-1-one oxime |

| Compound No.15-17 | (E)-3-(benzo[d][1,3]dioxol-5-yl)acrylic acid ester O-R' |

| Compound No. | R¹ |
|---|---|
| 15 | -CH₂-C(=O)-NH-(2,3-dihydrobenzo[b][1,4]dioxin-6-yl) |
| 16 | -CH₂-C(=O)-NH-CH₂-(2,4-dichlorophenyl) |
| 17 | -CH₂-C(=O)-NH-(2,3-dimethylcyclohexyl) |

FIG. 6-4
| Compound No. | R¹ | R² | R³ |
|---|---|---|---|
| 26 | H | H | 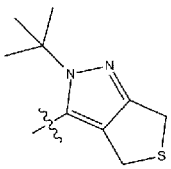 |
| 27 |  | H | 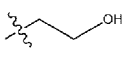 |
| 28 | H | H |  |
| 29 | H | H | 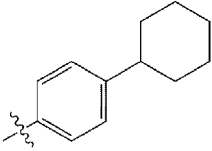 |
| 30 | H | H | 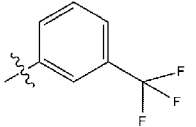 |
| 31 | H | H | 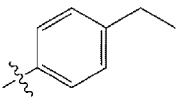 |
| 32 | H | H | 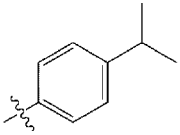 |
| 33 | H | H | H |
| 34 | H | H | 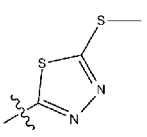 |

| Compound No. | R¹ | R² | R³ | R⁴ |
|---|---|---|---|---|
| 48 | —O—CH₂CH₃ | O | N | —CH₂—(4-Cl-phenyl) |
| 49 | H | S | S | —CH₂—C(=O)—NH—(2,5-dihydrothiophene-1,1-dioxide) |
| 50 | H | S | O | CH₃ |
| 51 | H | O | N | —CH₂—C(=O)—OH |
| 52 | —O—CH₃ | O | N | —CH₂—(3,4-diCl-phenyl) |

Compound No.53

Compound No.54

Compound No.55

FIG. 6-9

| Compound No. | R¹ | R² | R³ |
|---|---|---|---|
| 61 | H | H | –O–C(=O)–O–CH₂CH₃ (ethoxycarbonylmethoxy) |
| 62 | H | H | OH |
| 63 | H | CH₃ | OH |
| 64 | H | H | –O–CH₂–C(=O)–N(H)–CH(COOH)–CH₂–COOH |
| 65 | Br | H | OH |

| Compound No. | R¹ | R² |
|---|---|---|
| 66 | NO₂ | H |
| 67 | H | Br |
| 68 | H | H |

FIG. 6-12

| Compound No. | R¹ |
|---|---|
| 83 | ⸺O⸺CH₃ |
| 84 | ⸺O⸺CH₂CH₃ |
| 85 | OH |

| | |
|---|---|
| Compound No.86 | (3-hydroxy-2-(benzo[d][1,3]dioxol-5-yl)-4H-chromen-4-one structure) |
| Compound No.87 | (2-(benzo[d][1,3]dioxol-5-yl)-3-carboxy-7-methoxy-1-methyl-4-oxo-1,4-dihydroquinoline structure) |
| Compound No.88-90 | (benzo[d][1,3]dioxolo-fused quinolin-2(1H)-one core with R¹ and R² substituents) |

| Compound No. | R¹ | R² |
|---|---|---|
| 88 | CH₃ | ⸺S⸺CH₂CH₂CH₂CH₃ |
| 89 | CH₃ | ⸺S⸺CH₂CH₂OH |
| 90 | H | ⸺CH₂⸺N(CH₂CH₂OH)(C(=O)-3-fluorophenyl) |

FIG. 7

| Compound No. | Concentration (μM) | % Inhibition | Compound No. | Concentration (μM) | % Inhibition |
|---|---|---|---|---|---|
| 1 | 50 | 100.8 | 51 | 250 | 96.0 |
| 2 | 10 | 89.8 | 52 | 50 | 95.9 |
| 3 | 50 | 99.4 | 53 | 250 | 119.3 |
| 4 | 25 | 104.7 | 54 | 250 | 85.9 |
| 5 | 10 | 99.9 | 55 | 250 | 100.3 |
| 6 | 100 | 89.1 | 56 | 250 | 120.4 |
| 7 | 25 | 95.5 | 57 | 250 | 87.8 |
| 8 | 10 | 98.8 | 58 | 50 | 77.3 |
| 9 | 10 | 95.5 | 59 | 250 | 96.2 |
| 10 | 250 | 96.8 | 60 | 250 | 83.1 |
| 11 | 250 | 75.3 | 61 | 250 | 107.4 |
| 12 | 250 | 95.3 | 62 | 250 | 81.0 |
| 13 | 250 | 85.9 | 63 | 250 | 81.6 |
| 14 | 250 | 98.8 | 64 | 250 | 97.3 |
| 15 | 250 | 75.3 | 65 | 250 | 98.6 |
| 16 | 250 | 77.3 | 66 | 250 | 83.6 |
| 17 | 250 | 82.9 | 67 | 250 | 81.1 |
| 18 | 250 | 87.5 | 68 | 250 | 108.1 |
| 19 | 250 | 88.1 | 69 | 250 | 80.8 |
| 20 | 250 | 89.9 | 70 | 250 | 92.7 |
| 21 | 250 | 77.6 | 71 | 250 | 98.1 |
| 22 | 250 | 85.6 | 72 | 250 | 85.1 |
| 23 | 250 | 104.1 | 73 | 250 | 82.0 |
| 24 | 250 | 88.1 | 74 | 250 | 82.6 |
| 25 | 250 | 100.2 | 75 | 250 | 87.3 |
| 26 | 250 | 92.2 | 76 | 250 | 116.9 |
| 27 | 250 | 85.8 | 77 | 250 | 80.0 |
| 28 | 250 | 96.0 | 78 | 250 | 81.2 |
| 29 | 250 | 92.7 | 79 | 250 | 90.4 |
| 30 | 250 | 83.7 | 80 | 250 | 77.2 |
| 31 | 250 | 89.2 | 81 | 250 | 97.1 |
| 32 | 250 | 93.1 | 82 | 250 | 78.6 |
| 33 | 250 | 94.0 | 83 | 250 | 78.9 |
| 34 | 50 | 98.6 | 84 | 50 | 90.8 |
| 35 | 250 | 90.4 | 85 | 50 | 85.9 |
| 36 | 250 | 81.3 | 86 | 250 | 94.0 |
| 37 | 50 | 98.7 | 87 | 250 | 99.4 |
| 38 | 50 | 89.3 | 88 | 250 | 92.1 |
| 39 | 250 | 89.2 | 89 | 250 | 95.9 |
| 40 | 250 | 98.9 | 90 | 250 | 82.4 |
| 41 | 250 | 76.9 | 91 | 250 | 83.3 |
| 42 | 250 | 96.4 | 92 | 250 | 83.1 |
| 43 | 250 | 82.4 | 93 | 250 | 92.6 |
| 44 | 250 | 116.9 | 94 | 250 | 79.8 |
| 45 | 250 | 97.7 | | | |
| 46 | 250 | 99.8 | | | |
| 47 | 250 | 83.5 | | | |
| 48 | 250 | 96.6 | | | |
| 49 | 250 | 76.1 | | | |
| 50 | 250 | 98.0 | | | |

LACTATE DEHYDROGENASE INHIBITOR AND ANTIEPILEPTIC DRUG CONTAINING THE SAME

TECHNICAL FIELD

The present invention relates to a lactate dehydrogenase inhibitor and an antiepileptic drug containing isosafrole (or a derivative thereof) as an active ingredient.

BACKGROUND ART

Epilepsy is a neurological disorder caused by excessive excitation of electric activity in the brain and is diagnosed by a characteristic electroencephalogram (epileptic electroencephalogram). The prevalence of epilepsy is high, reaching about 1% of the total population. Treatment methods for epilepsy mainly include drug therapy, and more than 20 types of therapeutic drugs for epilepsy are used in clinical settings (Non-Patent Document 1). However, it is known that these existing therapeutic drugs for epilepsy do not work for about 30% of patients with epilepsy. From such a background, therapeutic drugs for "refractory epilepsy" for which existing drugs do not work are currently needed.

Since epilepsy is caused by excessive neural excitation, therapeutic drugs for epilepsy are mostly targeted to molecules that control electrical activity. Specific examples include ion channels, synaptic receptors, and neurotransmitter transporters (Non-Patent Document 2). On the other hand, it is clinically known that "diet therapy" called ketogenic diet treatment is effective for some epilepsy patients for whom these existing drugs do not work (Non-Patent Document 3). Recently, anti-epileptic mechanisms mediated by the ketogenic diet have been revealed one after another (Non-Patent Documents 4 to 6). That is, if a drug acting on the energy metabolic pathway is developed, it is promising as a drug for refractory epilepsy.

Stiripentol (CAS: 49763-96-4, 4-dimethyl-1-[(3, 4-methylenedioxy)-phenyl]-1-penten-3-ol, see formula (I) below) is an antiepileptic drug. Stiripentol was first developed as a brain disease drug (Patent Document 1), and it was then shown to be effective for Dravet syndrome (one of childhood epilepsies) which is one of refractory epilepsies (Non-Patent Documents 7 and 8). Stiripentol is now clinically used as a drug for Dravet syndrome in Europe (approved in 2007) and Japan (approved in 2012) under the trade name of Diacomit. However, although stiripentol therapy was successful in Dravet syndrome, it has not been successful at present in clinical trials for other epilepsies (especially adult epilepsies) (Non-Patent Document 9).

Recently, it has been reported that stiripentol is an inhibitor of lactate dehydrogenase (LDH) (Patent Document 2). Lactate dehydrogenase is a "metabolic enzyme" existing "on the energy metabolic pathway" and carrying out interconversion between lactate and pyruvate. Lactate dehydrogenase inhibitors themselves have been developed mainly for the purpose of development of antimalarial drugs (Non-Patent Documents 10 and 11), and development of anticancer drugs (Non-Patent Documents 12 and 13). However, it is unknown whether these lactate dehydrogenase inhibitors have antiepileptic effects. That is, at this time, stiripentol is the only "antiepileptic drug" having "lactate dehydrogenase inhibitory action".

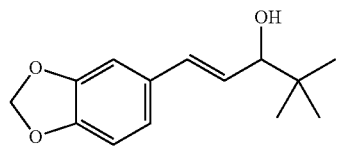

(I)

RELATED ART REFERENCES

Patent Documents

Patent Document 1: U.S. Pat. No. 3,910,959
Patent Document 2: WO2014/115764

Non-Patent Documents

Non-Patent Document 1: Sirven et al, Mayo Clin Proc 87: 879-889, 2012
Non-Patent Document 2: Meldrum et al, Neurotherapeutics 4: 18-61, 2007
Non-Patent Document 3: Neal et al, Lancet Neurol 7: 500-506, 2008
Non-Patent Document 4: Ma et al, J Neurosci 27: 3618-3625, 2007
Non-Patent Document 5: Juge et al, Neuron 68: 99-112, 2010
Non-Patent Document 6: Masino et al, J Clin Invest 121: 2679-2683, 2011
Non-Patent Document 7: Perez et al, Epilepsia 40: 1618-1626, 1999
Non-Patent Document 8: Chiron et al, Lancet 356: 1638-1642, 2000
Non-Patent Document 9: Chiron, Neurotherapeutics 4: 123-125, 2007
Non-Patent Document 10: Deck et al, J Med Chem 41: 3879-3887, 1998
Non-Patent Document 11: Cameron et al, J Biol Chem 279: 31429-31439, 2004
Non-Patent Document 12: Granchi et al, J Med Chem 54: 1599-1612, 2011
Non-Patent Document 13: Farabegoli et al, Eur J Pharm Sci 47: 729-738, 2012
Non-Patent Document 14: Aboul-Enein et al, Eur J Med Chem 47: 360-369, 2012
Non-Patent Document 15: Riban et al, Neuroscience 112: 101-111, 2002
Non-Patent Document 16: Houser, Brain Res 535: 195-204, 1990
Non-Patent Document 17: Shen et al, Epilepsy Res 7: 40-48, 1990

SUMMARY OF THE INVENTION

Problems to be Solved by the Invention

Stiripentol has an aromatic allyl alcohol structure and has a chemical structure not found in conventional antiepileptic drugs (Patent Document 1). Moreover, stiripentol is the only compound as "antiepileptic drug having lactic dehydrogenase inhibitory action" (Patent Document 2). Antiepileptic drugs acting on metabolic pathways (metabolic enzymes) are promising as a therapeutic drug for refractory epilepsy. However, although stiripentol is effective for some childhood refractory epilepsies (Dravet syndrome), it is not used for other refractory epilepsies. Thus, by maintaining the lactate dehydrogenase inhibitory activity and modifying the chemical structure of stiripentol, it is expected that "antiepileptic drugs" can be developed which are also effective for refractory epilepsies for which stiripentol is not effective. In addition, such antiepileptic drugs have very high industrial utility value.

However, it is not easy to assume at the current technological level how to alter the chemical structure to make stiripentol effective for refractory epilepsies for which stiripentol is not effective. Therefore, an object of the present invention is to provide an antiepileptic drug having "lactate dehydrogenase inhibitory action" and also effective for refractory epilepsies for which stiripentol is not effective.

Means for Solving the Problems

The present inventors hypothesized that "hydroxy group at the 3-position" (Patent Document 1) which characterizes stiripentol (aromatic allyl alcohol) and "functional group at the 3-position" reported in the prior art (Non-Patent Document 14) are rather unnecessary. Therefore, they focused on isosafrole (CAS: 120-58-1, 5-(1-propenyl)-1, 3-benzodioxole, see formula (II) below) which is a substance obtained by removing the hydroxy group and the tertiary butyl group from the 3-position of stiripentol. They have revealed that this isosafrole has an inhibitory action on lactate dehydrogenase. In addition, they identified a number of "lactate dehydrogenase inhibitors having isosafrole as a scaffold" with a completely different chemical structure from stiripentol. Moreover, they found that inhibitors of lactate dehydrogenase such as isosafrole remarkably suppressed adult refractory epilepsy (medial temporal lobe epilepsy associated with hippocampal sclerosis) which can not be suppressed by stiripentol, thereby completing the present invention.

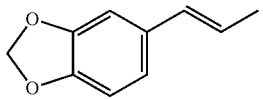

(II)

In one aspect, the present invention provides the following invention:
[1] A lactate dehydrogenase inhibitor containing a compound represented by formula (III).

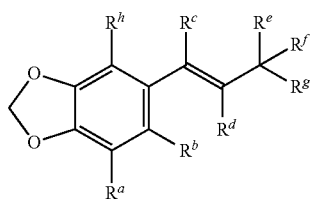

(III)

wherein
$R^a$ represents a hydrogen atom, a halogen atom or alkoxy optionally substituted with halogen atoms;
$R^b$ represents a hydrogen atom, a halogen atom, alkoxy optionally substituted with halogen atoms or nitro, or represents a group which together with $R^c$, $R^d$ or $R^g$ forms a ring structure optionally having substituents;

$R^c$ represents a hydrogen atom or carboxyl, or represents a group which together with $R^b$, $R^e.R^f$ or $R^g$ forms a ring structure optionally having substituents;
$R^d$ represents a hydrogen atom or —$X^{11}$—$R^{11}$, or represents a group which together with $R^b$ or $R^g$ forms a ring structure optionally having substituents;
 $X^{11}$ represents alkylene, —NH—CO—, —$CH_2$—$NR^{12}$—CO— or —S—;
 $R^{11}$ represents aryl optionally having substituents, carboxyl, alkyl optionally substituted with halogen atoms, or hydroxyalkyl;
 $R^{12}$ represents hydroxyalkyl;
for $R^e$, $R^f$ and $R^g$:
 (i) all represent a hydrogen atom; or
 (ii) $R^e$ and $R^f$ together represent =O, =$NR^{21}$ or =$CR^{21}R^{22}$, and $R^g$ represents a hydrogen atom, —$X^{31}$—$R^{31}$, —O—$X^{32}$—$R^{32}$, —N(—$X^{33}$—$R^{33}$)(—$X^{34}R^{34}$), —$CR^{35}R^{36}R^{37}$;
 $R^{21}$ represents hydroxy, or represents a group which together with $R^c$ or $R^g$ forms a ring structure optionally having substituents;
 $R^{22}$ represents nitro, or aminocarbonyl in which a hydrogen atom bound to a nitrogen atom may be substituted with alkyl;
 $X^{31}$ represents a single bond, alkenylene, —$CH_2$—O—$CH_2$—CO—NH—, —$CH_2$—O—$CH_2$—CO— or —CO—;
 $R^{31}$ represents aryl optionally having substituents, heteroaryl optionally having substituents, cycloalkyl optionally having substituents, heterocyclic amino optionally having substituents, hydroxy, alkoxy optionally substituted with halogen atoms, or hydroxyalkyl;
 wherein, when $X^{31}$ is a single bond and $R^{31}$ is heterocyclic amino optionally having substituents, the single bond is bound to an atom other than the nitrogen atom of the heterocyclic amino;
 $X^{32}$ represents a single bond or —$CH_2$—CO—NH—;
 $R^{32}$ represents aryl optionally having substituents, heteroaryl optionally having substituents, cycloalkyl optionally having substituents or alkyl optionally substituted with halogen atoms;
 $X^{33}$ and $X^{34}$ each independently represent a single bond, alkylene, —$CH_2$—CO—NH— or —$SO_2$—;
 $R^{33}$ and $R^{34}$ each independently represent a hydrogen atom, aryl optionally having substituents, heteroaryl optionally having substituents, cycloalkyl optionally having substituents, hydroxylalkyl, carboxyl, alkyl optionally substituted with halogen atoms or alkynyl group, or represent a group which together with $R^b$, $R^c$, $R^d$ or $R^e.R^f$ forms a ring structure optionally having substituents, or $R^{33}$ and $R^{34}$, together with the nitrogen atom to which they are bound through $X^{33}$ and $X^{34}$ which are single bonds, represent heterocyclic amino optionally having substituents;
 $R^{35}$, $R^{36}$ and $R^{37}$ each independently represent a hydrogen atom or —$X^{31}$—$R^{31}$, or represent a group which together with $R^b$, $R^c$, $R^d$ or $R^e.R^f$ forms a ring structure optionally having substituents;
 $R^h$ represents a hydrogen atom or a halogen atom;
 wherein the number of the ring structure formed by binding between $R^b$ and $R^c$, the ring structure formed by binding between $R^b$ and $R^d$, the ring structure formed by binding between $R^b$ and $R^g$, the ring structure formed by binding between $R^c$ and $R^e.R^f$, the ring structure formed by binding between $R^c$ and $R^g$, the ring structure formed by binding between $R^d$ and $R^g$, or the ring structure formed by binding between $R^e.R^f$ and $R^g$ formed in formula (III) is no more than one.

[2] The lactate dehydrogenase inhibitor described in [1], wherein the compound represented by formula (III) is a compound in which $R^c$, $R^d$, $R^e$, $R^f$, and $R^g$ are all hydrogen atoms.

[3] The lactate dehydrogenase inhibitor described in [1], wherein the compound represented by formula (III) is isosafrole represented by formula (II).

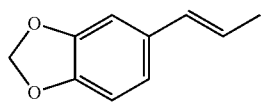

[4] The lactate dehydrogenase inhibitor described in [1], wherein the compound represented by formula (III) is a compound in which any of the ring structure formed by binding between $R^b$ and $R^c$, the ring structure formed by binding between $R^b$ and $R^d$, the ring structure formed by binding between $R^b$ and $R^g$, the ring structure formed by binding between $R^c$ and $R^e.R^f$, the ring structure formed by binding between $R^c$ and $R^g$, the ring structure formed by binding between $R^d$ and $R^g$, and the ring structure formed by binding between $R^e.R^f$ and $R^g$ is not formed.

[5] The lactate dehydrogenase inhibitor described in [1], wherein the compound represented by formula (III) is a compound in which any one of the ring structure formed by binding between $R^b$ and $R^c$, the ring structure formed by binding between $R^b$ and $R^d$, the ring structure formed by binding between $R^b$ and $R^g$, the ring structure formed by binding between $R^c$ and $R^e.R^f$, the ring structure formed by binding between $R^c$ and $R^g$, the ring structure formed by binding between $R^d$ and $R^g$, and the ring structure formed by binding between $R^e.R^f$ and $R^g$ is formed.

[6] An antiepileptic drug containing the lactate dehydrogenase inhibitor described in any one of [1] to [5] as active ingredient.

Effect of the Invention

Stiripentol is the only "antiepileptic drug" having "lactate dehydrogenase inhibitory action" (Patent Documents 1 and 2). However, stiripentol is clinically effective only for some childhood refractory epilepsy (Dravet syndrome). We newly found isosafrole as a second "antiepileptic drug" having "lactate dehydrogenase inhibitory action". Isosafrole dramatically inhibited refractory epilepsy to which stiripentol is ineffective (medial temporal lobe epilepsy, an adult refractory epilepsy). In addition, we have also discovered a number of lactate dehydrogenase inhibitors having isosafrole as a scaffold. Thus, isosafrole and derivatives of isosafrole are industrially available as a therapeutic agent for epilepsy.

BRIEF DESCRIPTION OF THE DRAWINGS

FIGS. 6-1 to 6-13 show compounds having isosafrole as a scaffold, which have a stronger inhibitory effect on lactate dehydrogenase compared with that of isosafrole (see Examples). Compounds exhibiting 100% (±25%) inhibition rate (% Inhibition) at 250 μM or less are shown.

FIG. 7 shows inhibitory concentrations (μM) against lactate dehydrogenase and their inhibition rate (% Inhibition) for the compounds having isosafrole as a scaffold as shown in FIG. 6 (see Examples).

MODE FOR CARRYING OUT THE INVENTION

Figure 1:
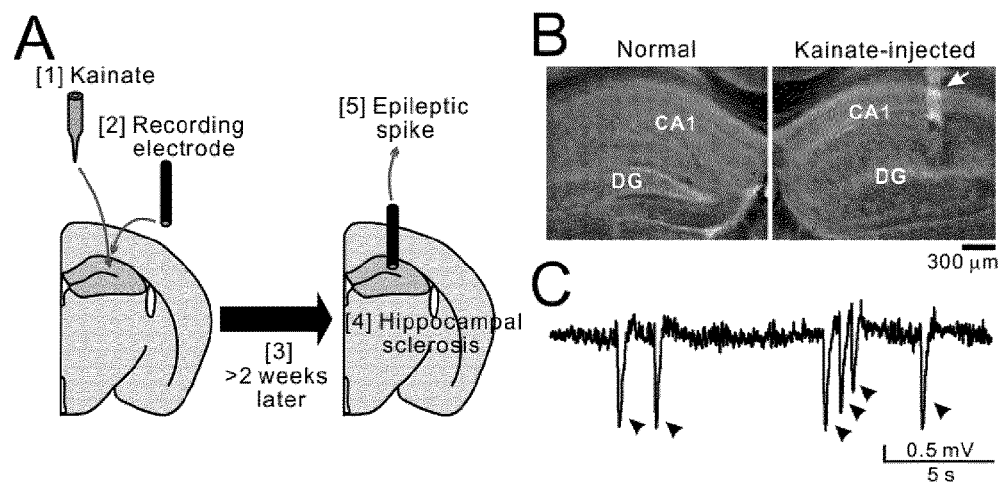
FIG. 1 shows a hippocampal sclerosis model mouse (see Examples).
A: Preparation method of hippocampal sclerosis model mouse. B: Morphology of normal hippocampus (left) and hippocampus exhibiting hippocampal sclerosis (right). The white arrow indicates a trace of recording electrode. C: Epileptic spikes recorded from hippocampal sclerosis model mouse (arrowhead).

The present invention provides lactate dehydrogenase inhibitors described in (a) and pharmaceuticals containing the same as an active ingredient described in (b) below.

(a) A lactate dehydrogenase inhibitor containing isosafrole or a compound having isosafrole as a scaffold (also herein referred to as "isosafrole analog").

(b) An antiepileptic drug containing the lactate dehydrogenase inhibitor described in (a) as an active ingredient.

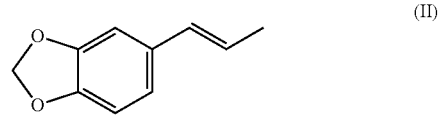

As shown in formula (II), isosafrole has a chemical structure in which a 1-propenyl group is attached to the 5-position of 1,3-benzodioxole which is an aromatic ring. The formula (II) representing isosafrole corresponds to the case where all of $R^a$, $R^b$, $R^c$, $R^d$, $R^e$, $R^f$, $R^g$ and $R^h$ in formula (III) are represented by hydrogen atoms.

On the other hand, examples of the compound containing isosafrole as a scaffold (isosafrole analog) include, for example, those in which the propenyl group is modified and those in which 1,3-benzodioxole, an aromatic ring, is functionalized. However, the compound is not particularly limited as long as it is a compound having isosafrole as a scaffold and has a lactate dehydrogenase inhibitory activity, and can be used as an antiepileptic drug.

Isosafrole and isosafrole analogs are compounds which can be represented by formula (III). Although several stereoisomers of the compound represented by formula (III) may exist, any of the stereoisomers are included. In the present invention, a mixture (racemate) of a plurality of stereoisomers may be used or a purified product of any of stereoisomers may be used as a lactate dehydrogenase inhibitor, and further as an active ingredient of an antiepileptic drug. Those skilled in the art could appropriately judge which of the racemate and each stereoisomer should be used, through testing the effectiveness of each stereoisomer as needed and taking purification costs into consideration.

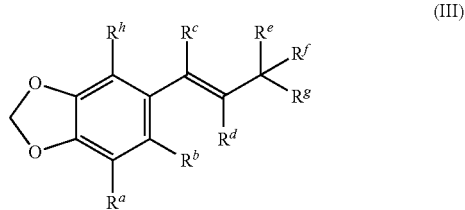

(III)

The definitions of the symbols included in formula (III) are as follows. Specific examples and other explanations of the terms used in the definitions of certain symbols (for example, halogen atom at $R^a$) apply equally to the same terms used in the definitions of other symbols (for example, halogen atom at $R^b$).

$R^a$ represents a hydrogen atom, a halogen atom or alkoxy optionally substituted with halogen atoms.

Examples of the halogen atom include fluorine (F), chlorine (Cl), bromine (Br) and iodine (I).

Examples of the alkoxy group include groups derived from lower alcohols having about 1 to 4 carbon atoms, such as methoxy (—OCH$_3$) and ethoxy (—OC$_2$H$_5$). In the alkoxy group, part or all of hydrogen atoms may be substituted with halogen atoms or may not be substituted at all. The alkyl group moiety in the alkoxy group may be linear or branched.

$R^b$ represents a hydrogen atom, a halogen atom, alkoxy optionally substituted with halogen atoms or nitro (—NO$_2$), or represents a group which together with $R^c$, $R^d$ or $R^g$ forms a ring structure optionally having substituents.

$R^c$ represents a hydrogen atom or carboxyl (—COOH), or represents a group which together with $R^b$, $R^e$.$R^f$ or $R^g$ forms a ring structure optionally having substituents.

The carboxyl group may be in the form of a carboxylate anion (—COO$^-$).

$R^d$ represents a hydrogen atom or —X$^{11}$—R$^{11}$, or represents a group which together with $R^b$ or $R^g$ forms a ring structure optionally having substituents.

$X^{11}$ represents alkylene, —NH—CO—, —CH$_2$—NR$^{12}$—CO— or —S—.

Examples of the alkylene group include divalent groups derived from lower alkyl groups having about 1 to 6 carbon atoms, such as methylene (—CH$_2$—) and ethylene (—C$_2$H$_5$—).

$R^{11}$ represents aryl optionally having substituents, carboxyl, alkyl optionally substituted with halogen atoms, or hydroxyalkyl.

Examples of the aryl group include phenyl (—C$_6$H$_5$) and naphthyl (—C$_{10}$H$_9$).

Examples of the substituent of the aryl group include a halogen atom, alkyl optionally substituted with halogen atoms, alkoxy optionally substituted with halogen atoms, hydroxy, thioalkoxy (—SR), carboxyl, aryl optionally having substituents, heteroaryl optionally having substituents, and cycloalkyl optionally having substituents. The number of substituents and the site to which the substituent is introduced are optionally selected and can be appropriately selected depending on the nature of the substituent.

Examples of the alkyl group include lower alkyl groups having about 1 to 6 carbon atoms such as methyl, ethyl, propyl, butyl, pentyl and octyl. The alkyl group may be linear (n-alkyl) or branched (i-, sec-, tert-alkyl). In the alkyl group, part or all of hydrogen atoms may be substituted with halogen atoms or may not be substituted at all.

Examples of the hydroxyalkyl group include groups derived from lower alcohols having about 1 to 4 carbon atoms, such as oxymethyl (—CH$_2$OH) and oxyethyl (—C$_2$H$_5$OH). The alkyl group moiety in the hydroxyalkyl group may be linear or branched. The number and the site of the hydroxy groups are optionally selected.

$R^{12}$ represents hydroxyalkyl.

$R^e$ and $R^f$ each independently represent a hydrogen atom, hydroxy or alkyl optionally substituted with a halogen atom, or together represent =O, =NR$^{21}$, =CR$^{21}$R$^{22}$.

$R^{21}$ represents hydroxy, or represents a group which together with $R^e$ or $R^g$ forms a ring structure optionally having substituents.

$R^{22}$ represents nitro, or aminocarbonyl in which two hydrogen atoms bound to a nitrogen atom may be each independently substituted with alkyl.

$R^g$ represents a hydrogen atom, —X$^{31}$—R$^{31}$, —O—X$^{32}$—R$^{32}$, —N(—X$^{33}$—R$^{33}$) (—X$^{34}$—R$^{34}$), —CR$^{35}$R$^{36}$R$^{37}$.

$X^{31}$ represents a single bond, alkenylene, —CH$_2$—O—CH$_2$—CO—NH—, —CH$_2$—O—CH$_2$—CO— or —CO—.

Examples of the alkenylene group include divalent groups derived from lower alkenyl groups having about 2 to 6 carbon atoms, such as 1-propenylene (—CH=CH—CH$_2$—) and 2-propenylene (—CH—CH=CH$_2$—). The number and the position of the carbon-carbon double bonds are optionally selected.

$R^{31}$ represents aryl optionally having substituents, heteroaryl optionally having substituents, cycloalkyl optionally having substituents, heterocyclic amino optionally having substituents, hydroxy, alkoxy optionally substituted with halogen atoms, or hydroxyalkyl;

When $X^{31}$ is a single bond and $R^{31}$ is heterocyclic amino optionally having substituents, the single bond is bound to an atom other than the nitrogen atom of the heterocyclic amino (this provision is for avoiding duplication of —X$^{31}$—R$^{31}$ with —N(—X$^{33}$—R$^{33}$) (—X$^{34}$—R$^{34}$) when "R$^{33}$ and R$^{34}$, together with the nitrogen atom to which they are bound through X$^{33}$ and X$^{34}$ which are single bonds, represent heterocyclic amino optionally having substituents" as will be described later).

Examples of the heteroaryl group include pyridyl (—C$_5$H$_5$N), pyrazinyl (—C$_4$H$_3$N$_2$), triazinyl (—C$_3$H$_2$N$_3$), tetrazinyl (—C$_2$HN$_4$), pyrrolyl (—C$_4$H$_4$N), thienyl (—C$_4$H$_3$S), furanyl (—C$_4$H$_3$O), 1,3-benzodioxole, a group possessed by Compound No. 26, and a group possessed by Compound No. 34. Regarding examples, the number and the position of substituents possessed by the heteroaryl group, the same thing as the above-mentioned substituent possessed by aryl can be said.

Examples of the cycloalkyl group include those having about 1 to 6 carbon atoms such as cyclopropyl, cyclobutyl, cyclopentyl and cyclohexyl. Regarding examples, the number and the position of substituents possessed by the cycloalkyl group, the same thing as the above-mentioned substituent possessed by aryl can be said.

Examples of the heterocyclic amino group include pyrrolidinyl (—$C_4H_8N$), piperidinyl (—$C_5H_{10}N$), piperazinyl (—$C_4H_9N_2$), and a group possessed by the Compound No. 70 (see FIG. 6-10). Regarding examples, the number and the position of substituents optionally possessed by the heterocyclic amino group, the same thing as the above-mentioned substituent possessed by aryl can be said. For example, when the heterocyclic amino group is piperazinyl, examples of the substituent include phenyl optionally having a substituent (such as a halogen atom or a halogenated alkyl group).

$X^{32}$ represents a single bond or —$CH_2$—CO—NH—.

$R^{32}$ represents aryl optionally having substituents, heteroaryl optionally having substituents, cycloalkyl optionally having substituents or alkyl optionally substituted with halogen atoms.

$X^{33}$ and $X^{34}$ each independently represent a single bond, alkylene, —$CH_2$—CO—NH— or —$SO_2$—.

$R^{33}$ and $R^{34}$ each independently represent a hydrogen atom, aryl optionally having substituents, heteroaryl optionally having substituents, cycloalkyl optionally having substituents, hydroxylalkyl, carboxyl, alkyl optionally substituted with halogen atoms or alkynyl group, or represent a group which together with $R^b$, $R^c$, $R^d$ or $R^e.R^f$ forms a ring structure optionally having substituents, or $R^{33}$ and $R^{34}$, together with the nitrogen atom to which they are bound through $X^{33}$ and $X^{34}$ which are single bonds, represent heterocyclic amino optionally having substituents.

Examples of the alkynyl group include lower alkynyl groups having about 2 to 6 carbon atoms such as 2,3-propynyl (—$CH_2$—C≡CH). The number and the position of the carbon-carbon triple bonds are optionally selected.

When $R^g$ represented by —N(—$X^{33}$—$R^{33}$) (—$X^{34}$—$R^{34}$)) is a group which together with $R^b$, $R^c$, $R^d$ or $R^e.R^f$ forms a ring structure, one of —$X^{33}$—$R^{33}$ and —$X^{34}$—$R^{34}$ may be linked with $R^b$, $R^c$, $R^d$ or $R^e.R^f$ to form the ring structure, and the other (particularly, other than a hydrogen atom) may be in a form corresponding to a substituent bonded to N contained in the ring structure (Compound No. 57 (see FIG. 6-8) and Compound No. 91 (see FIG. 6-13)), or a form may be taken such that —$X^{33}$—$R^{33}$ and —$X^{34}$—$R^{34}$ together with $R^b$, $R^c$, $R^d$ or $R^e.R^f$ form a ring structure (Compound No. 55 (see FIG. 6-7), which includes a double bond derived from $R^{33}$ and $R^{34}$).

$R^{35}$, $R^{36}$ and $R^{37}$ each independently represent a hydrogen atom or —$X^{31}$—$R^{31}$, or represent a group which together with $R^b$, $R^c$, $R^d$ or $R^e.R^f$ forms a ring structure optionally having substituents.

When $R^g$ represented by —$CR^{35}R^{36}R^{37}$ is a group which together with $R^b$, $R^c$, $R^d$ or $R^e.R^f$ forms a cyclic structure, one or two of $R^{35}$, $R^{36}$ and $R^{37}$ may be linked with $R^b$, $R^c$, $R^d$ or $R^e.R^f$ to form the ring structure, and the remainings group (particularly, other than a hydrogen atom) may be in a form corresponding to a substituent bonded to C contained in the cyclic structure (Compound No. 54 (see FIG. 6-7), which includes a double bond derived from $R^{35}$ and $R^{36}$ and a substituent derived from $R^{37}$; Compound Nos. 59 and 60 (see FIG. 6-8), which include two bonds in the quinuclidine structure derived from $R^{35}$ and $R^{36}$, respectively). Similarly, when $R^g$ represented by —$CR^{35}R^{36}R^{37}$ is a group which together with $R^b$, $R^c$, $R^d$ or $R^e.R^f$ forms a ring structure such as condensed ring, one or two selected from $R^{35}$, $R^{36}$ and $R^{37}$ are linked with $R^b$, $R^c$, $R^d$ or $R^e.R^f$ as described above to form a part of the ring structure (one side of the condensed ring), and the remaining groups may represent groups which link to one of the atoms forming the backbone of the ring structure to form a further part of the ring structure (the other side of the condensed ring) (Compound Nos. 61 to 65 (see FIG. 6-9)).

$R^h$ represents a hydrogen atom or a halogen atom.

Only at most one of the following is formed in formula (III): a ring structure formed by binding between $R^b$ and $R^c$, a ring structure formed by binding between $R^b$ and $R^d$, a ring structure formed by binding between $R^b$ and $R^g$, a ring structure formed by binding between $R^c$ and $R^e.R^f$ ($R^{21}$ of =$NR^{21}$ or =$CR^{21}R^{22}$), a ring structure formed by binding between $R^c$ and $R^g$ ($R^{33}$ or $R^{34}$ of —N(—$X^{33}$—$R^{33}$)(—$X^{34}$—$R^{34}$), or $R^{35}$, $R^{36}$ or $R^{37}$ of —$CR^{35}R^{36}R^{37}$), a ring structure formed by binding between $R^d$ and $R^g$, a ring structure formed by binding between $R^e.R^f$ and $R^g$. That is, for example, a ring structure formed by binding between $R^b$ and $R^c$ and a ring structure formed by binding between $R^b$ and $R^d$ are not formed at the same time, and in the case where the former is formed, $R^d$ represents a hydrogen atom or —$X^{11}$—$R^{11}$ (a group forming a ring structure together with $R^b$ is not represented).

When $R^g$ is a hydrogen atom, $R^e$ and $R^f$ are also limited to hydrogen atoms. That is, the definition that $R^g$ is a hydrogen atom is intended to include, in the compound represented by the formula (III), isosafrole and derivatives thereof in which $R^e$, $R^f$ and $R^g$ are all hydrogen atoms. Stiripentol, which is in a combination of $R^e$ being hydroxy, $R^f$ being alkyl (t-butyl) and $R^g$ being a hydrogen atom, is not included in the compound represented by the formula (III).

Specific examples of the compound represented by formula (III) include the compounds (Nos. 1 to 94) listed in FIGS. 6-1 to 6-13. Among them, compounds having a predetermined ring structure ($Ring_{bc}$, $Ring_{bd}$, $Ring_{bg}$, $Ring_{cef}$, $Ring_{cg}$, $Ring_{dg}$ or $Ring_{efg}$) are Nos. 44 to 94 (see the corresponding table below), and compounds having no ring structure are Nos. 1 to 43. Any of the Compound Nos. 1 to 94 and the other compounds represented by the formula (III) can be obtained or synthesized according to known methods by one skilled in the art.

TABLE 1

| Ring structure | Compound No. |
| --- | --- |
| none | 1-13, 14, 15-17, 18-34, 35-38, 39, 40-43 |
| $R^b$ and $R^c$ together form a ring structure ($Ring_{bc}$) (see formula III-bc) | 93, 94 |
| $R^b$ and $R^d$ together form a ring structure ($Ring_{bd}$) (see formula III-bd) | 92 |
| $R^b$ and $R^g$ together form a ring structure ($Ring_{bg}$) (see formula III-bg) $R^g$: —N(—$X^{33}$—$R^{33}$)(—$X^{34}$—$R^{34}$) | 88-90, 91 |
| $R^c$ and $R^e•R^f$ together form a ring structure ($Ring_{cef}$) (see formula III-cef) | 69-81, 82 |
| $R^c$ and $R^g$ together form a ring structure ($Ring_{cg}$) (see formula III-cg) $R^g$: —$CR^{35}R^{36}R^{37}$ | 83-85, 86, 87 |
| $R^d$ and $R^g$ together form a ring structure ($Ring_{dg}$) (see formula III-dg) $R^g$: —N(—$X^{33}$—$R^{33}$)(—$X^{34}$—$R^{34}$) $R^g$: —O—$X^{32}$—$R^{32}$ $R^g$: —$CR^{35}R^{36}R^{37}$ | 45-47, 48-52, 55, 56, 57, 58, 66-68 53 54, 59, 60, 61-65, |
| $R^e•R^f$ and $R^g$ together form a ring structure ($Ring_{efg}$) (see formula III-efg) $R^g$: —N(—$X^{33}$—$R^{33}$)(—$X^{34}$—$R^{34}$) | 44 |

One preferred embodiment of the present invention includes isosafrole or an analog thereof, which is close to the original structure of isosafrole, wherein all of $R^e$, $R^f$ and $R^g$ are hydrogen atoms, and wherein $R^c$ and $R^d$ are also hydrogen atoms. That is, compounds are preferred, wherein the carbon atom at the 3-position of the propenyl group in formula (III), and further the carbon atoms at the 1-position and the 2-position are not modified, and wherein only the 1,3-benzodioxole portion may be modified ($R^a$, $R^b$, $R^h$ may be other than a hydrogen atom).

As one preferred embodiment of the present invention, embodiments wherein $R^e$ and $R^f$ together represent =O, =NR$^{21}$ or =CR$^{21}$R$^{22}$ and wherein $R^g$ represents —X$^{31}$—R$^{31}$, —O—X$^{32}$—R$^{32}$, —N—(—X$^{33}$—R$^{33}$) (—X$^{34}$—R$^{34}$) or —CR$^{35}$R$^{36}$R$^{37}$ are preferred, and among them, particularly preferred are embodiments wherein $R^e$ and $R^f$ together represent =O, to which many compounds belong.

One preferred embodiment of the present invention includes isosafrole analogs in which none of the following are formed in formula (III): a ring structure formed by binding between $R^b$ and $R^c$, a ring structure formed by binding between $R^b$ and $R^d$, a ring structure formed by binding between $R^b$ and $R^g$, a ring structure formed by binding between $R^c$ and $R^e$.$R^f$, a ring structure formed by binding between $R^c$ and $R^g$, a ring structure formed by binding between $R^d$ and $R^g$, a ring structure formed by binding between $R^e$.$R^f$ and $R^g$. Specific examples of such isosafrole analogs are isosafrole and Compound Nos. 1 to 44.

One preferred embodiment of the present invention includes isosafrole analogs in which any of the following is formed in formula (III): a ring structure formed by binding between $R^b$ and $R^c$, a ring structure formed by binding between $R^b$ and $R^d$, a ring structure formed by binding between $R^b$ and $R^g$, a ring structure formed by binding between $R^c$ and $R^e$.$R^f$, a ring structure formed by binding between $R^c$ and $R^g$, a ring structure formed by binding between $R^d$ and $R^g$, a ring structure formed by binding between $R^e$.$R^f$ and Rg.

When $R^b$ and $R^c$ form a ring structure, formula (III) can also be described as formula (III-bc) below. In the formula (III-bc), the $R^{bc}$ group which is connected via dotted lines to each of the carbon atom on 1,3-benzodioxole originally bound with $R^b$ and the carbon atom on the propenyl group originally bound with $R^c$ represents a group in which $R^b$ and $R^c$ together form a ring structure (Ring$_{bc}$) optionally having substituents, and the definitions of the other symbols are the same as those in the formula (III).

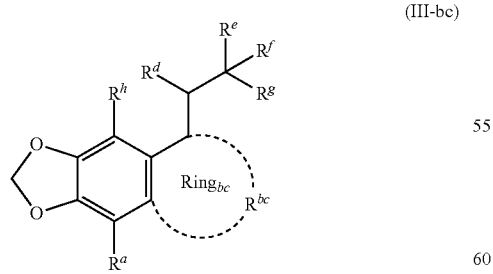

(III-bc)

When $R^b$ and $R^d$ form a ring structure, formula (III) can also be described as formula (III-bd) below. In the formula (III-bd), the $R^{bd}$ group which is connected via dotted lines to each of the carbon atom on 1,3-benzodioxole originally bound with $R^b$ and the carbon atom on the propenyl group originally bound with $R^d$ represents a group in which $R^b$ and $R^d$ together form a ring structure (Ring$_{bd}$) optionally having substituents, and the definitions of the other symbols are the same as those in the formula (III).

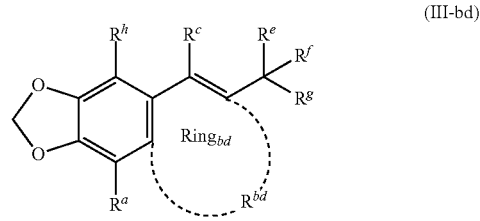

(III-bd)

When $R^b$ and $R^g$ form a ring structure, formula (III) can also be described as formula (III-bg) below. In the formula (III-bg), the $R^{bg}$ group which is connected via dotted lines to each of the carbon atom on 1,3-benzodioxole originally bound with $R^b$ and the carbon atom on the propenyl group originally bound with $R^g$ represents a group in which $R^b$ and $R^g$ together form a ring structure (Ring$_{bg}$) optionally having substituents, and the definitions of the other symbols are the same as those in the formula (III).

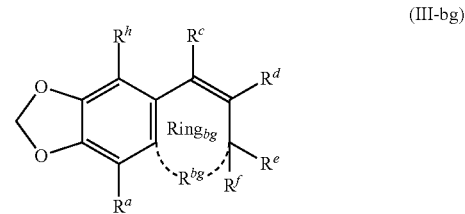

(III-bg)

When $R^c$ and $R^e$.$R^f$ form a ring structure, formula (III) can also be described as formula (III-cef) below. In the formula (III-cef), the $R^{cef}$ group which is connected via dotted lines to each of the carbon atoms on the propenyl group originally bound with $R^c$ and $R^g$ represents a group in which $R^c$ and $R^e$.$R^f$ together form a ring structure (Ring$_{cef}$) optionally having substituents, and the definitions of the other symbols are the same as those in the formula (III).

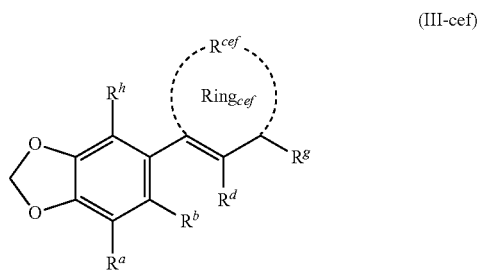

(III-cef)

When $R^c$ and $R^g$ form a ring structure, formula (III) can also be described as formula (III-cg) below. In the formula (III-cg), the $R^{cg}$ group which is connected via dotted lines to each of the carbon atoms on the propenyl group originally bound with $R^c$ and $R^g$ represents a group in which $R^c$ and $R^g$ together form a ring structure (Ring$_{cg}$) optionally having substituents, and the definitions of the other symbols are the same as those in the formula (III).

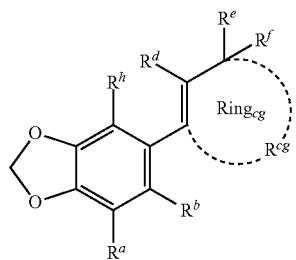
(III-cg)

When $R^d$ and $R^g$ form a ring structure, formula (III) can also be described as formula (III-dg) below. In the formula (III-dg), the $R^{dg}$ group which is connected via dotted lines to each of the carbon atoms on the propenyl group originally bound with $R^d$ and $R^g$ represents a group in which $R^d$ and $R^g$ together form a ring structure ($Ring_{dg}$) optionally having substituents, and the definitions of the other symbols are the same as those in the formula (III).

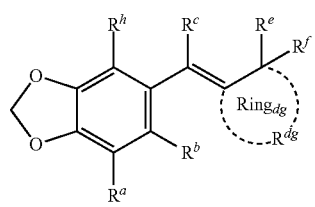
(III-dg)

When $R^e.R^f$ and $R^g$ form a ring structure, formula (III) can also be described as formula (III-efg) below. In the formula (III-efg), the $R^{efg}$ group which is connected via dotted lines to each of the carbon atoms on the propenyl group originally bound with $R^e.R^f$ and $R^g$ represents a group in which $R^e.R^f$ and $R^g$ together form a ring structure ($Ring_{efg}$) optionally having substituents, and the definitions of the other symbols are the same as those in the formula (III).

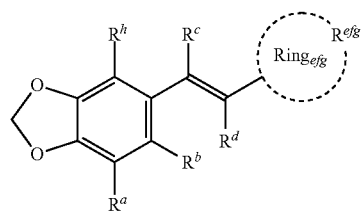
(III-efg)

$R^{bc}$, $R^{bd}$, $R^{bg}$, $R^{cef}$, $R^{cg}$, $R^{dg}$ and $R^{efg}$ each contain at least one carbon atom, nitrogen atom, oxygen atom or sulfur atom as atoms forming part of the backbone of $Ring_{bc}$, $Ring_{bd}$, $Ring_{bg}$, $Ring_{cef}$, $Ring_{cg}$, $Ring_{dg}$ and $Ring_{efg}$, respectively. Each ring (ring structure) is preferably a five-membered ring, a six-membered ring, a seven-membered ring or a condensed ring thereof (Compound Nos. 59 and 60 (FIG. 6-8) (quinuclidine structure), Compounds 61 to 65 and 66 to 68 (FIG. 6-9), Compounds 86 and 87 (see FIG. 6-12)) or a spiro ring (Compound No. 94 (see FIG. 6-13)). The atoms forming the backbone of the ring structure may be connected through any of a single bond, a double bond, and a triple bond, and the ring structure may be aromatic or non-aromatic.

Each atom forming the backbone of the ring structure may be bound with a hydrogen atom or a halogen atom, or may be bound with a substituent. As the substituent possessed by the ring structure, for example, the above-described substituents exemplified as the substituents of the aryl group, an oxygen atom or nitrogen atom bonded through a double bond (Compound Nos. 48 to 52 (see FIGS. 6-6 and 6-7)), or other relatively large substituents (for example, groups represented as $R^1$ of Compound Nos. 45 to 47 and 58 (FIG. 6-6), groups represented as $R^4$ of Compound Nos. 48 to 52 (FIGS. 6-6 and 6-7), groups represented in Compound No. 55 (FIG. 6-7), groups represented in Compound No. 58 (FIG. 6-8), groups represented as $R^3$ of Compound Nos. 61 and 64 (see FIG. 6-9)) may be bound. A portion (branched portion) corresponding to such substituents is also included in a part of the groups each represented by $R^{bc}$, $R^{bd}$, $R^{bg}$, $R^{cef}$, $R^{cg}$, $R^{dg}$ and $R^{efg}$.

The type of epilepsy targeted by the pharmaceutical agent of the present invention is not particularly limited as long as it is epilepsy. In Examples, it is shown as an example that the pharmaceutical agent has an excellent antiepileptic effect on "medial temporal lobe epilepsy associated with hippocampal sclerosis" which is adult refractory epilepsy.

Pharmaceutical agents are usually prepared as pharmaceutical compositions. The pharmaceutical agents of the present invention may contain other drugs or functional compounds as necessary in addition to the active ingredient. For example, pharmaceutical agents containing other compounds that improve the in vivo pharmacokinetics of the active ingredient are contemplated. In addition, excipients, diluents, additives and the like necessary for preparing pharmaceutical agents may be contained.

The dosage form and administration method of the pharmaceutical agent are not particularly limited, and may be appropriately selected depending on the use of the pharmaceutical agent. Examples of the administration method include oral preparation and injection. For oral preparation, it can be selected from tablets, capsules, granules, powders or dry syrup, for example. Also, for injection, a formulation dissolved in an optional diluent (e.g., physiologic saline or dextrose solution) is contemplated.

The pharmaceutical agent of the present invention may be administered in an appropriate amount of active ingredient and at an appropriate number of times in consideration of, for example, the purpose, the age, gender, body weight of the subject to be administered (patient), severity of the disease and route of administration. A person skilled in the art such as doctor or pharmacist could determine the dose based on the state of each patient.

EXAMPLES

Method

Preparation and measurement of hippocampal sclerosis model mouse (FIGS. 1 to 3): The hippocampal sclerosis model mouse was prepared according to a previous literature (Non-Patent Document 15). Six to seven-week-old ICR mice were used for the experiment. Mice were fully anesthetized with a mixture of ketamine (100 mg/kg) and xylazine (20 mg/kg) and then set on a brain stereotaxic apparatus. Using a micro glass electrode and a Hamilton syringe from above the hippocampus of the head, a trace amount of kainate (0.8 nmol, 40 nL) for inducing epilepsy was injected into the dorsal hippocampus (1.6 mm behind the bregma, 1.6 mm laterally from the centerline, 1.4 mm deep from the brain surface), and then a metal electrode (a diameter of 200 µm) for epileptic electroencephalography was embedded near the kainic acid injection site. In addition, a small plastic U-shaped frame for head fixation required for in vivo electrical measurements was also attached to the head. After 2 weeks or more from surgery, epileptic spikes in the hippocampus were measured. The head was fixed via the U-shaped frame. Epileptic spikes were amplified, then measured via a band-pass filter (0.5-30 Hz) and taken into a computer using an AD converter. After measurement of the baseline electroencephalogram for 30 minutes, stiripentol (300 mg/kg), isosafrole (100-300 mg/kg), sodium oxamate (250-500 mg/kg), or physiological saline was intraperitoneally administered, and then further recording was conducted for 1 hour. Sodium oxamate was dissolved in water, and stiripentol and isosafrole were dissolved in sodium carboxymethyl cellulose (1%) and administered intraperitoneally. In data analysis, high-amplitude epilepsy spikes with an amplitude of 0.5 mV or more were counted 30 minutes before and after administration, respectively, and the efficacy was evaluated by normalization using the number of epileptic spikes before administration. In the observation of morphological changes due to hippocampal sclerosis, the brain was sliced to 300 µm thickness, fixed with 10% formalin, and stained with 0.05% cresylviolet.

Figure 4:
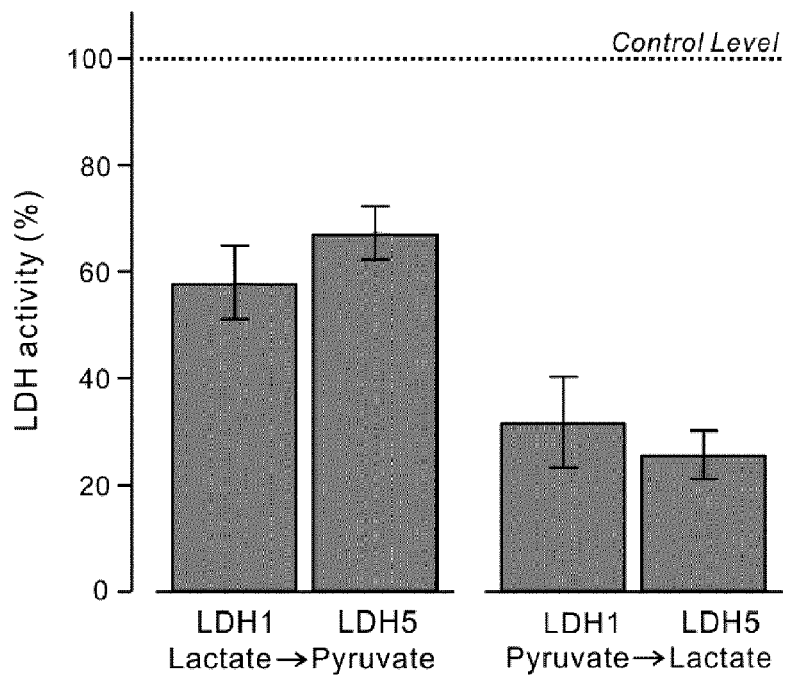
FIG. 4 shows inhibitory effects of isosafrole on enzymatic activities of lactate dehydrogenases (LDH-1 and LDH-5) (see Examples). The enzyme activity when isosafrole was absent (control value) was taken as 100%. That is, 0% indicates that lactate dehydrogenase is completely inhibited.

Evaluation of inhibition of lactate dehydrogenase by isosafrole (FIG. 4): The activity of lactate dehydrogenase was measured by a versatile method based on light absorption of NADH. Lactate dehydrogenase is an enzyme that interconverts pyruvate and lactate. At that time, NADH and NAD are also interconverted. For lactate dehydrogenase activity from lactate to pyruvate, lactate (20 mM), NAD (200 µM) and lactate dehydrogenase were added and the reaction rate of NADH produced was measured. On the other hand, for the lactate dehydrogenase activity from pyruvate to lactate, pyruvate (1.0 mM), NADH (200 µM) and lactate dehydrogenase were added and the reaction rate of decreasing NADH was measured. Both reactions were carried out at 37° C. in 100 mM sodium phosphate buffer (pH7.3). The light absorption of NADH at 340 nm was measured using an absorptiometer at 30 second intervals for 3.5 minutes to determine the reaction rate. Two kinds of human lactate dehydrogenase (human LDH-1 and LDH-5) were examined as lactate dehydrogenase. The amount of lactate dehydrogenase was set so that the maximum rates of the two lactate dehydrogenases were approximately the same: 0.0033 units/ml of LDH-1 and 0.01 units/ml of LDH-5 for the activity from lactate to pyruvate; and 0.0017 units/ml of LDH-1 and 0.0033 units/ml of LDH-5 for the activity from pyruvate to lactate. Isosafrole (500 µM) was added to these enzyme reaction systems to examine the inhibitory action of lactate dehydrogenase.

Identification of a lactate dehydrogenase inhibitor having isosafrole as a scaffold (FIGS. 5 to 7): Since NADH absorbs light in the ultraviolet region (340 nm) and many compounds absorb the wavelength, NADH is not suitable for screening using a compound library. Therefore, in order to evaluate the lactate dehydrogenase activity from pyruvate to lactate, pyruvate (100 µM), NADH (100 µM) and lactate dehydrogenase (0.015 U/mL of human LDH-5) were firstly added, then allowed to react in a 100 mM sodium phosphate buffer (pH7.3) at 37° C. for 60 minutes (LDH enzyme reaction, 200 µL/well). At this stage, the background absorbance at 492 nm was first measured with a plate reader (absorbance before coloring reaction). Next, in order to measure the amount of NADH remaining in the LDH enzyme reaction, 100 µL/well of a coloring solution in which diaphorase (25 U/mL) and INT (5 mM) were dissolved was added, and then allowed to react in a 100 mM sodium phosphate buffer (pH7.3) at 37° C. for 10 minutes (coloring reaction). Since INT changes to INT formazan by diaphorase in the presence of NADH and develops color, the absorbance at 492 nm of INT formazan was measured with a plate reader (absorbance after coloring reaction). In order to eliminate the influence of light absorption possessed by each compound itself, the value obtained by subtracting the absorbance before coloring reaction from the absorbance after coloring reaction was calculated as "absorbance change value ($\Delta A$)", and the inhibition rate was calculated from $\Delta A$.

Calculation of the inhibition rate (% Inhibition) is as follows. $\Delta A$ when the above reaction was carried out under the condition that lactate dehydrogenase was present was taken as "0% control value", and $\Delta A$ when the above reaction was carried out under the condition that lactate dehydrogenase was absent was taken as "100% control value". Under 0% control condition, low $\Delta A$ is shown because of the low amount of NADH remaining by LDH enzymatic reaction, whereas under 100% control condition LDH enzymatic reaction does not occur and high $\Delta A$ is shown. Then, the same reaction as the 0% control was carried out in the presence of a compound having isosafrole as a scaffold, and resultant $\Delta A$ was defined as "$\Delta A$ in the presence of the compound". If the tested compound has no inhibitory effect on lactate dehydrogenase, it shows a low $\Delta A$ close to the 0% control value, and if it has an inhibitory effect, it shows a high $\Delta A$ close to the 100% control value. Specifically, inhibition rate is calculated as follows: Inhibition rate (%)=100×($\Delta A$ in the presence of the compound–0% control value)/(100% control value–0% control value). Compounds showing inhibition rate of 100% (±25%) were described in FIGS. 6 and 7 as lactate dehydrogenase inhibitor.

Figure 5:
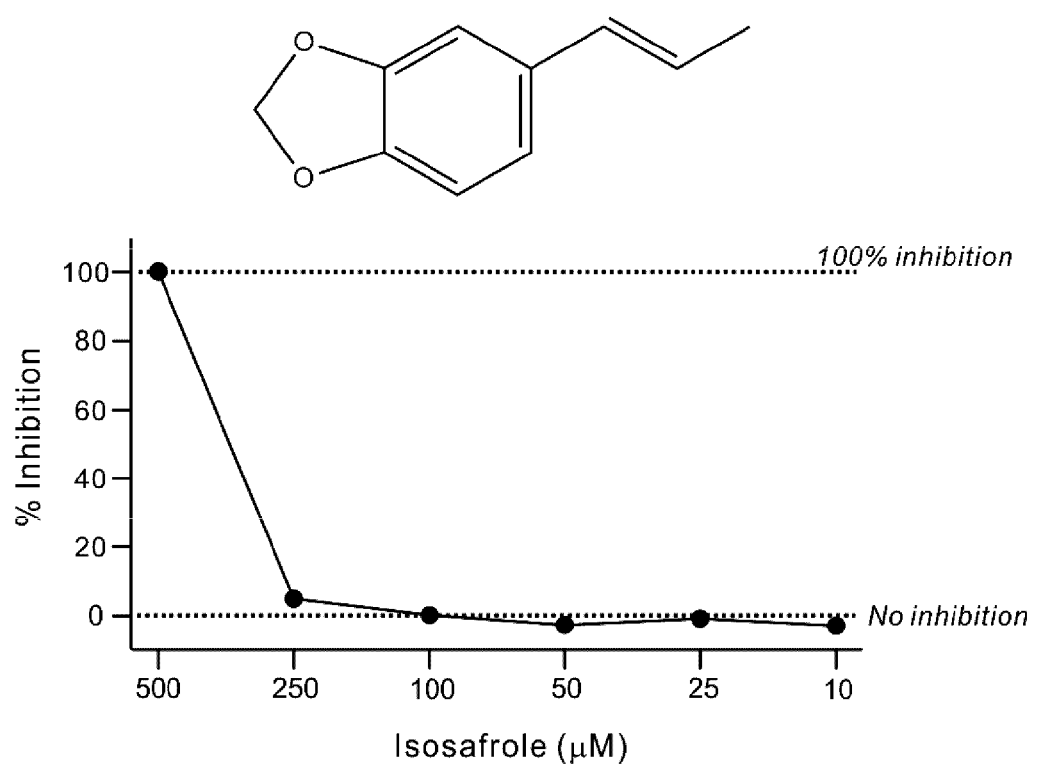
FIG. 5 shows a concentration dependence data on the inhibitory effect of isosafrole on the enzymatic activity of lactate dehydrogenase (LDH-5) (see Examples). The structural formula of isosafrole is shown in the upper row. The ordinate of the graph indicates the inhibition rate (% Inhibition), 100% indicates that lactate dehydrogenase is completely inhibited, and 0% indicates that lactate dehydrogenase is not inhibited at all. For calculation of inhibition rate, see Examples. Isosafrole inhibits lactate dehydrogenase at 500 μM but not at 250 μM.

Isosafrole and compounds having isosafrole as a scaffold (Nos. 1-94, see FIG. 6) were obtained from the following. Isosafrole and Compound No. 1 were obtained from Tokyo Chemical Industry, Compound Nos. 2-5 and Nos. 7-9 were obtained from Sigma, and Compound No. 6 was obtained from Bionet. For Compound Nos. 10-94, compound library of Platform for Drug Discovery, Informatics and Structural Life Science from the Ministry of Education, Culture, Sports, Science and Technology was used. For isosafrole, inhibition rates at each concentration of 500 µM to 10 µM as shown in FIG. 5 were calculated. For Compound Nos. 1-9, inhibition rates were calculated at 100, 50, 25, 10 µM, and the lowest concentrations showing the inhibition rate of 100±25% and the inhibition rates are shown in FIG. 7. For Compound Nos. 10-94, inhibition rates were calculated at 250 µM or 50 µM, and the concentrations used and the inhibition rates are shown in FIG. 7.

Results

Medial temporal lobe epilepsy with hippocampal sclerosis is a typical refractory epilepsy in adults (epilepsy for which existing drugs are not effective). First, according to a previous literature (Non-Patent Document 15), a trace amount of kainic acid was injected to a hippocampus to prepare hippocampal sclerosis model mouse (FIG. 1A). After 2 weeks or more from injection of kainic acid, morphological changes were observed in the hippocampus, the pyramidal cell layer became thin (FIG. 1B; CA1), and the dentate gyrus region became enlarged (FIG. 1B; DG). This is the same finding as the already reported hippocampal sclerosis model mouse (Non-Patent Document 15), which is similar to the symptom observed in human hippocampal sclerosis (Non-Patent Document 16). When recording on the hippocampus, spontaneous high-amplitude epileptic spikes were observed (FIG. 1C; arrowhead). That is, this hippocampal sclerosis model mouse is a chronic epilepsy model as reported in previous studies.

Then, stiripentol or isosafrole was intraperitoneally administered to this hippocampal sclerosis model mouse to examine the antiepileptic effect. The compound in which a hydroxy group and a tertiary butyl group at the 3-position are excluded from a pediatric antiepileptic drug stiripentol (FIG. $2A_1$) is isosafrole (FIG. $2B_1$). Epileptic spikes were scarcely inhibited by intraperitoneal administration of stiripentol (300 mg/kg) (FIG. $2A_2$). This is consistent with the fact that stiripentol is only used as an antiepileptic drug against childhood epilepsy (Dravet syndrome).

Figure 3:
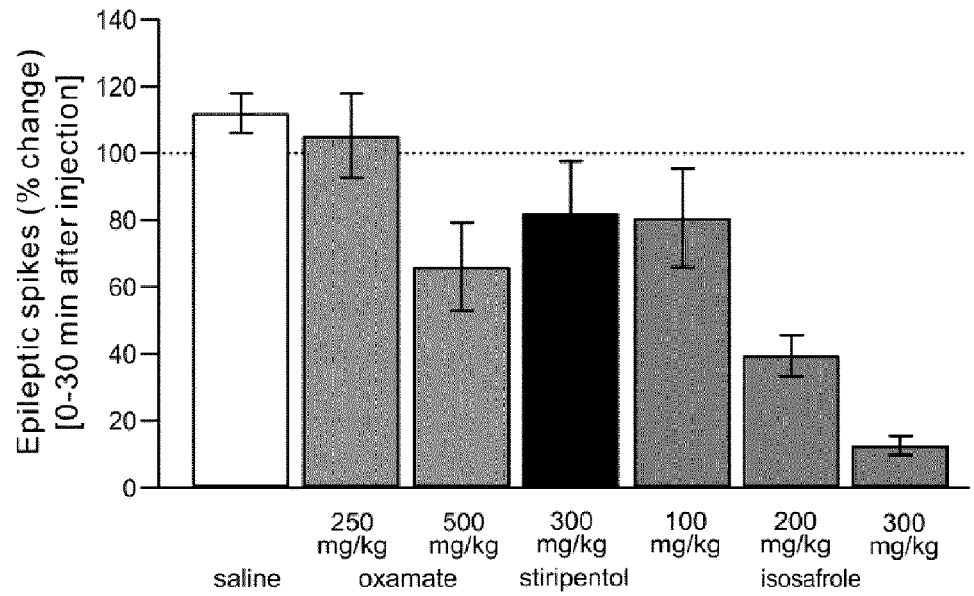
FIG. 3 shows a summary data on inhibitory effects of sodium oxamate, stiripentol and isosafrole on epileptic spikes of hippocampal sclerosis model mice (see Examples).

On the other hand, it was found that epileptic spikes can be significantly suppressed when isosafrole (300 mg/kg) is intraperitoneally administered (FIG. $2B_2$). Summary data on these antiepileptic effects are shown in FIG. 3. First, when sodium oxamate well known as a lactate dehydrogenase inhibitor was intraperitoneally administered, a weak antiepileptic effect was showed at 500 mg/kg (FIG. 3; saline, n=7; 250 mg/kg, N=7; 500 mg/kg, n=7). Previous studies have reported that when intraperitoneally administering stiripentol to rats at 300 mg/kg, drug-induced (pentylenetetrazole-induced) acute epileptic seizures were suppressed, and the plasma concentration at that time was 20-100 µg/ml (85-427 µM) (Non-Patent Document 17). However, intraperitoneal administration of stiripentol at 300 mg/kg showed little antiepileptic effect on this hippocampal sclerosis model mouse (FIG. 3; n=8). On the other hand, when isosafrole was intraperitoneally administered, a remarkable antiepileptic effect was observed at 200-300 mg/kg (FIG. 3; 100 mg/kg, n=8; 200 mg/kg, n=8; 300 mg/kg, n=8). These results indicate that isosafrole is an antiepileptic drug also effective for the refractory epilepsy model mouse.

Next, whether or not isosafrole has an inhibitory action against lactate dehydrogenase was examined by enzyme activity measurement. Enzyme activity in the presence of isosafrole (500 µM) was evaluated, assuming the enzyme activity of lactate dehydrogenation in the absence of isosafrole as 100%. Lactate dehydrogenase is composed of two subunits (LDHA and LDHB), LDH-5 is composed only of LDHA, and LDH-1 is composed only of LDHB. First, the effect of isosafrole on lactate dehydrogenase activity from lactate to pyruvate was investigated, and isosafrole was found to show an inhibitory effect on both human LDH-1 and LDH-5 (FIG. 4, Lactate→Pyruvate; LDH-1, n=4; LDH-5, n=4). In addition, the effect of isosafrole on lactate dehydrogenase activity from pyruvate to lactate was investigated. Then, it was also found that the enzyme activity in the direction of pyruvate→lactate was inhibited in both human LDH-1 and LDH-5, and its inhibitory effect was strong (FIG. 4, Pyruvate→Lactate; LDH-1, N=5; LDH-5, n=6). These results indicate that isosafrole is an inhibitor of lactate dehydrogenase.

Finally, we searched for compounds having inhibitory action on lactate dehydrogenase from among compounds having isosafrole as a scaffold. First, the inhibitory rate of lactate dehydrogenase (LDH-5) was examined at each concentration of isosafrole, and it was found that lactate dehydrogenase was inhibited at 500 µM, but not at 250 µM (FIG. 5). Therefore, we searched for inhibitors of lactate dehydrogenase inhibitors having isosafrole as the scaffold and a stronger effect than isosafrole. As a result, the following 94 compounds were identified as "compounds having isosafrole as a scaffold" which almost completely inhibited lactate dehydrogenase at 250 µM or less (FIG. 6 and FIG. 7).

Figure 2:
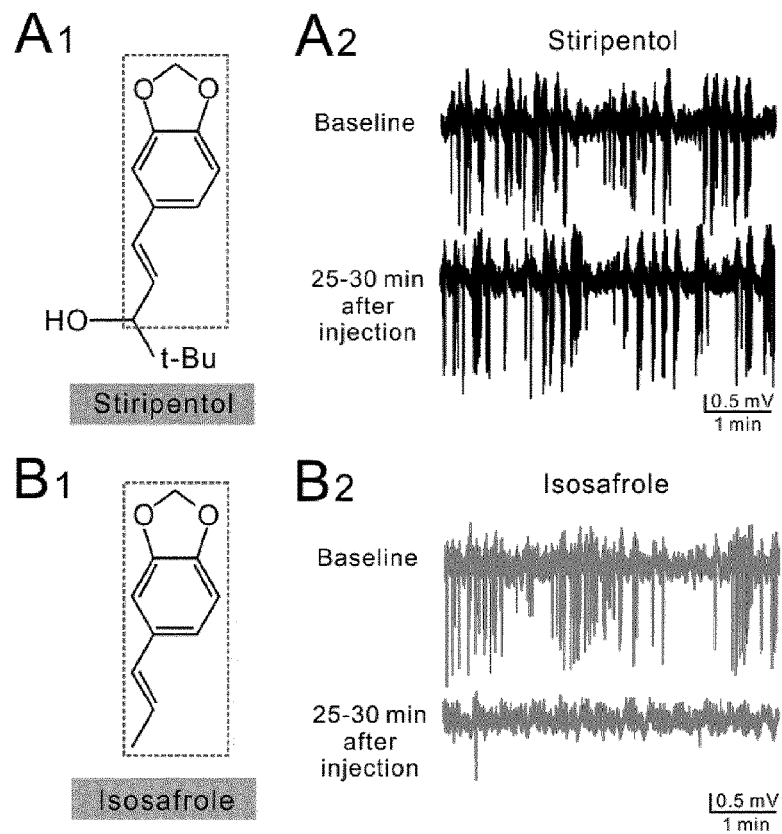
FIG. 2 shows effects of stiripentol and isosafrole on epileptic spikes of hippocampal sclerosis model mice (see Examples). A: Chemical structure of stiripentol ($A_1$) and effect of stiripentol on epileptic spikes ($A_2$). B: Chemical structure of isosafrole ($B_1$) and effect of isosafrole on epileptic spikes ($B_2$). Although almost no inhibitory effect by stiripentol is observed, isosafrole shows a remarkable inhibitory effect on epilepsy.
Figures 1, 6:
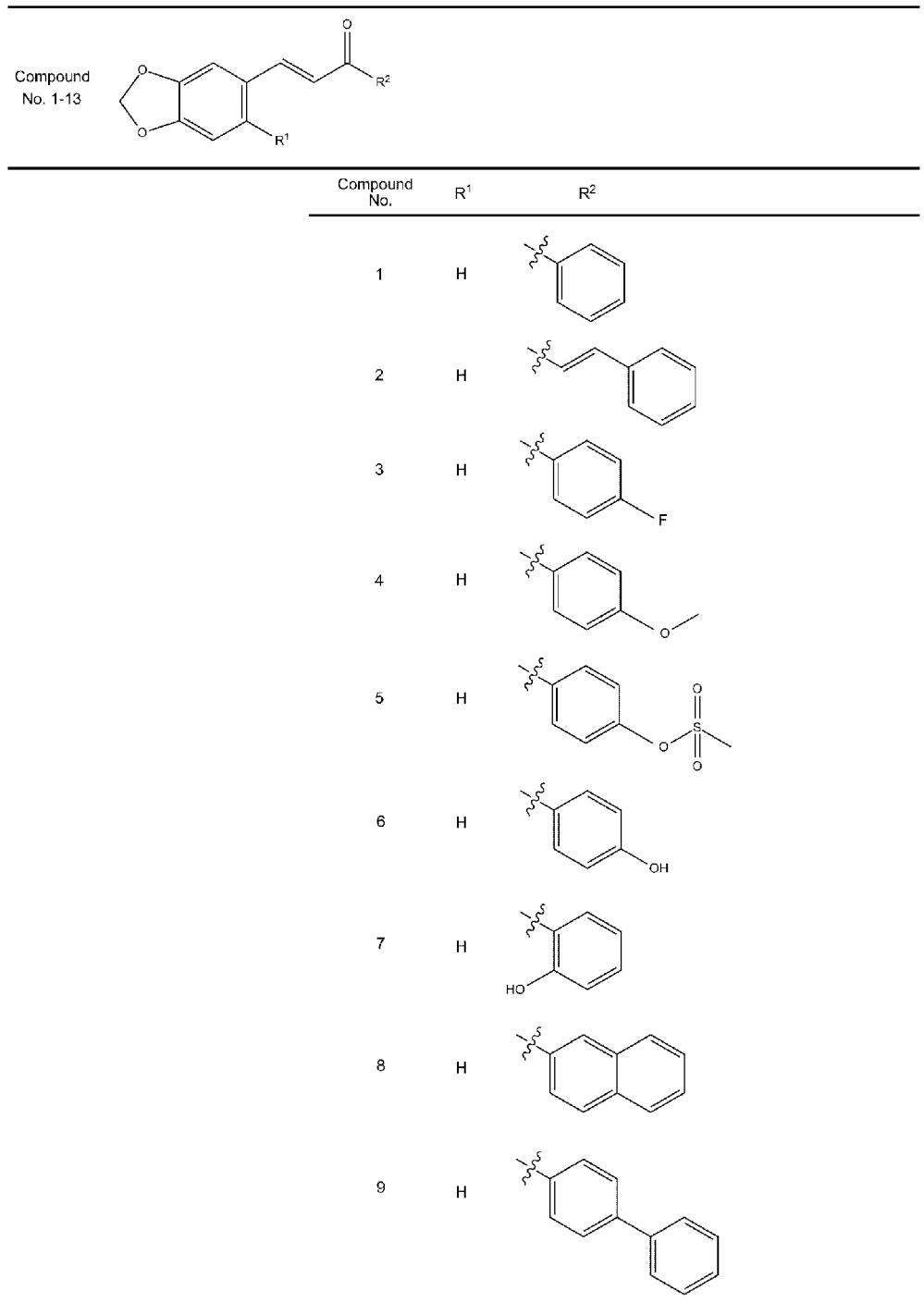
Figures 3, 6:
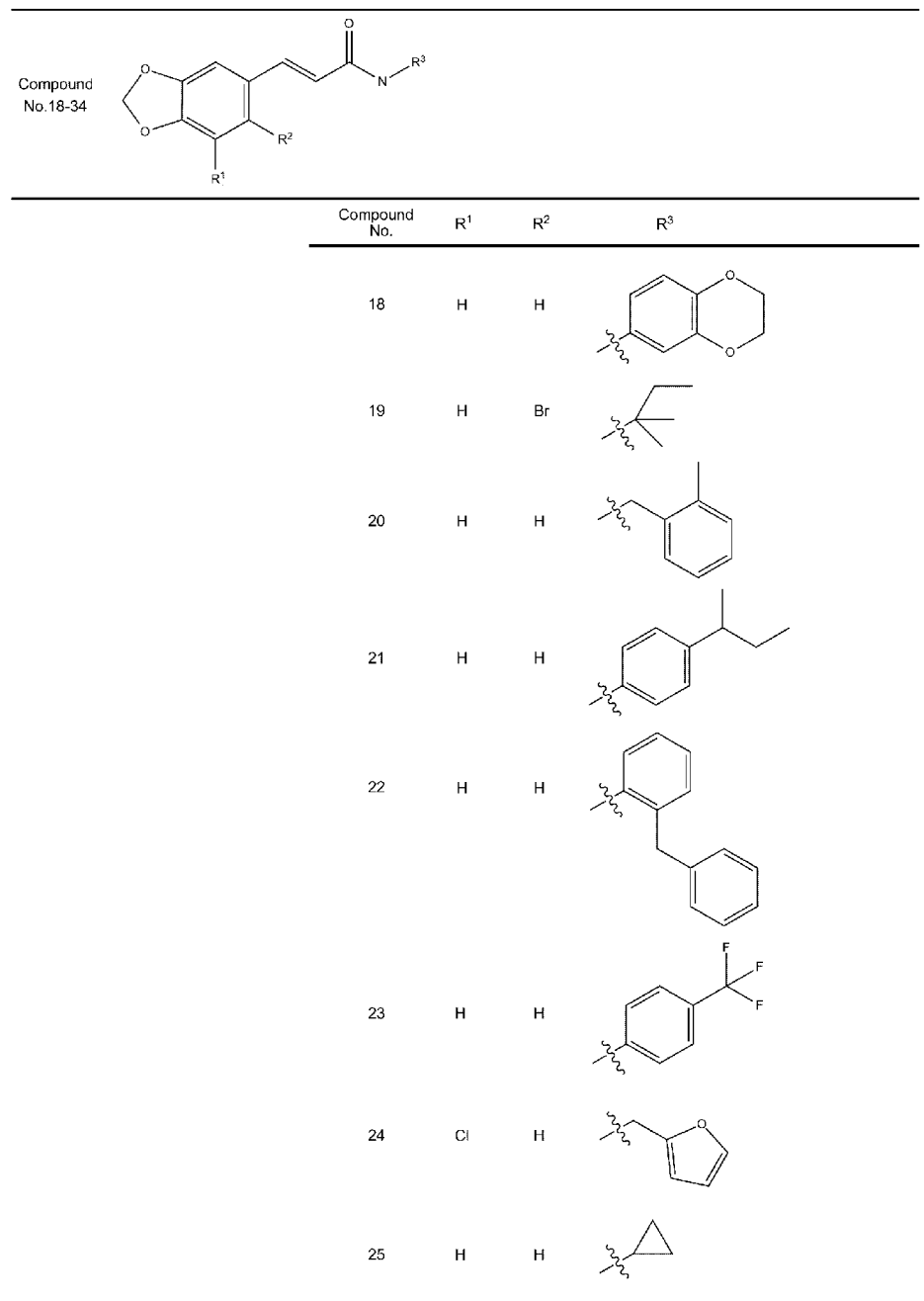
Figures 5, 6:
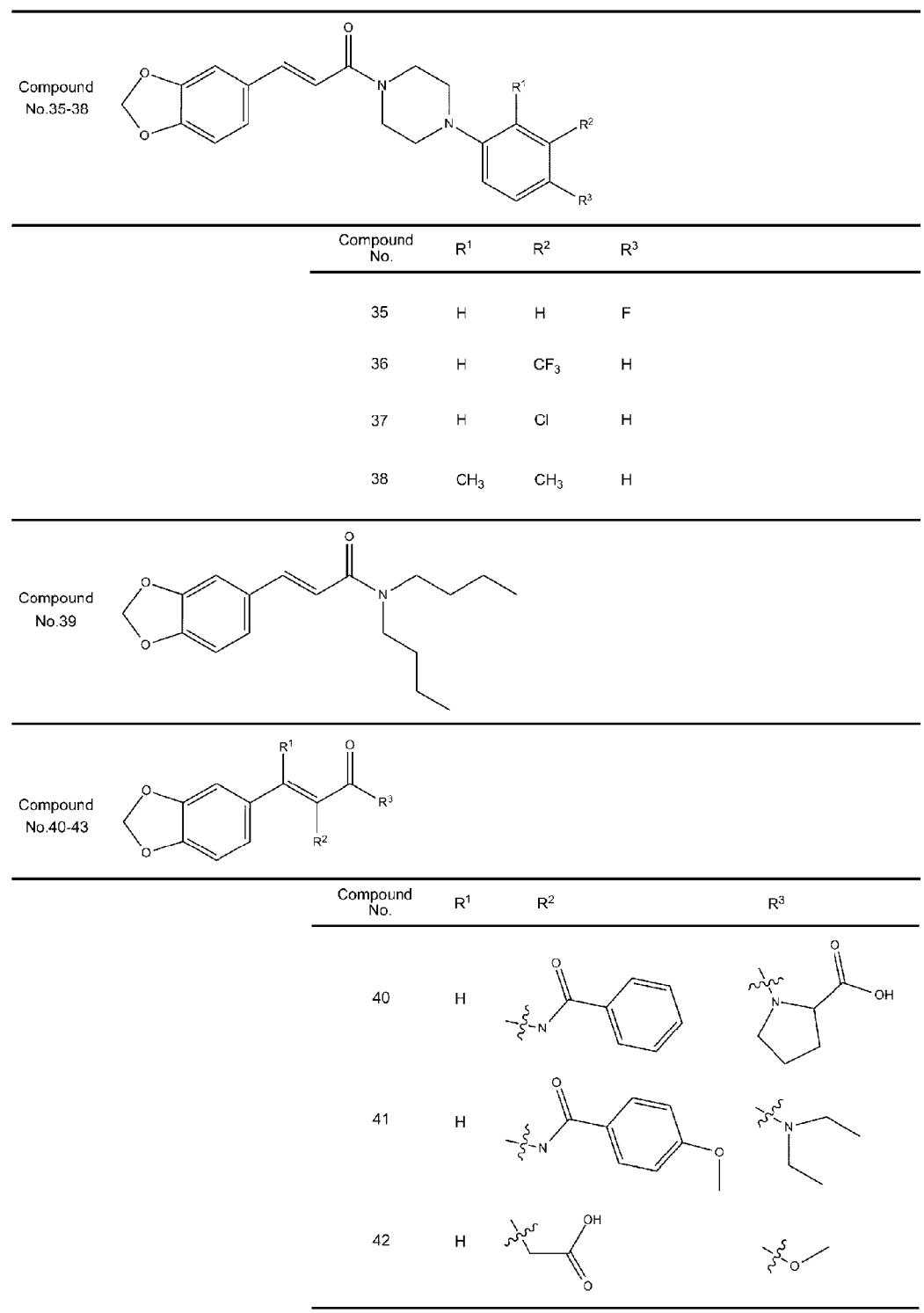
Figures 6, 7, 8:
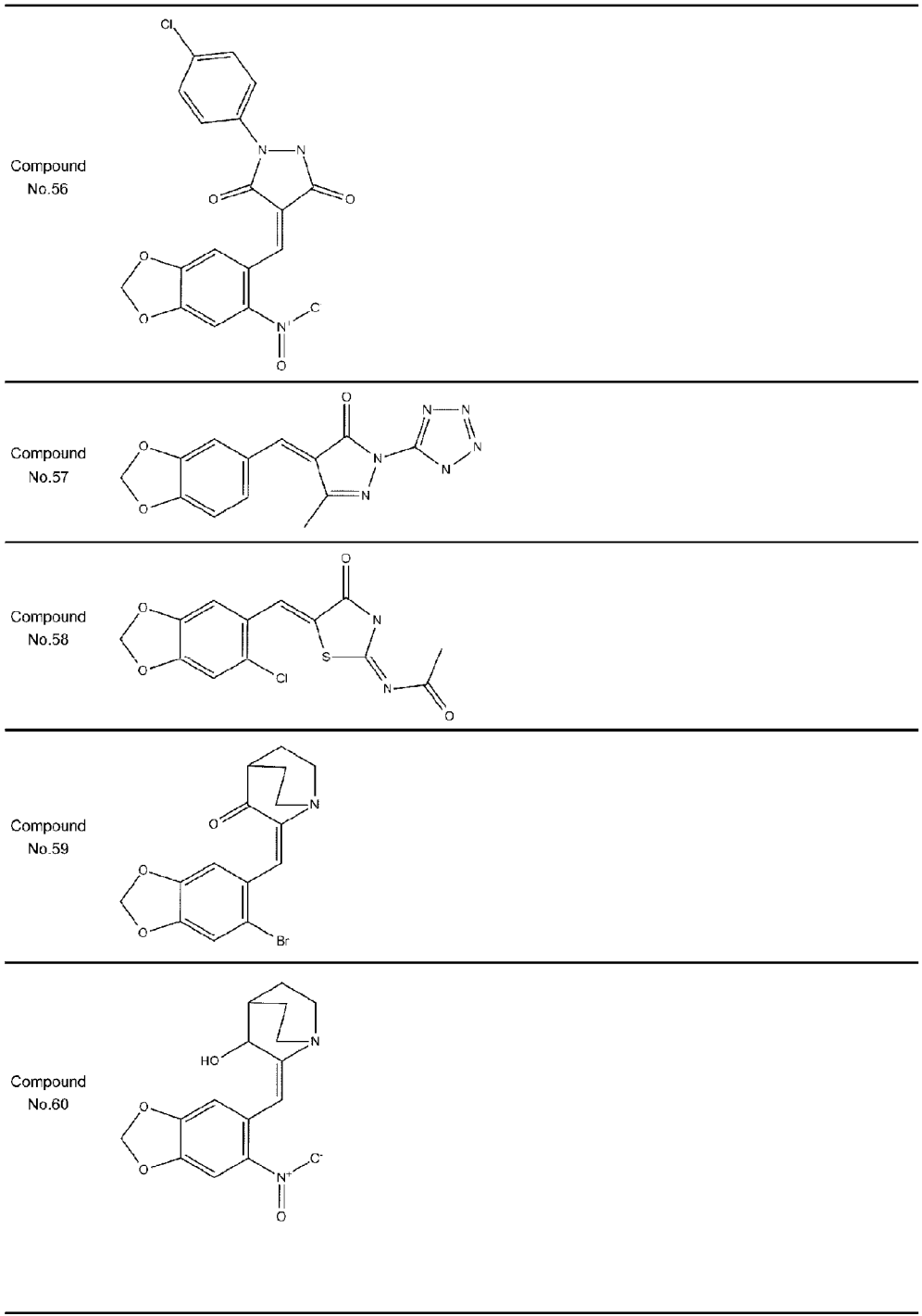
Figures 6, 7, 8, 9, 10:
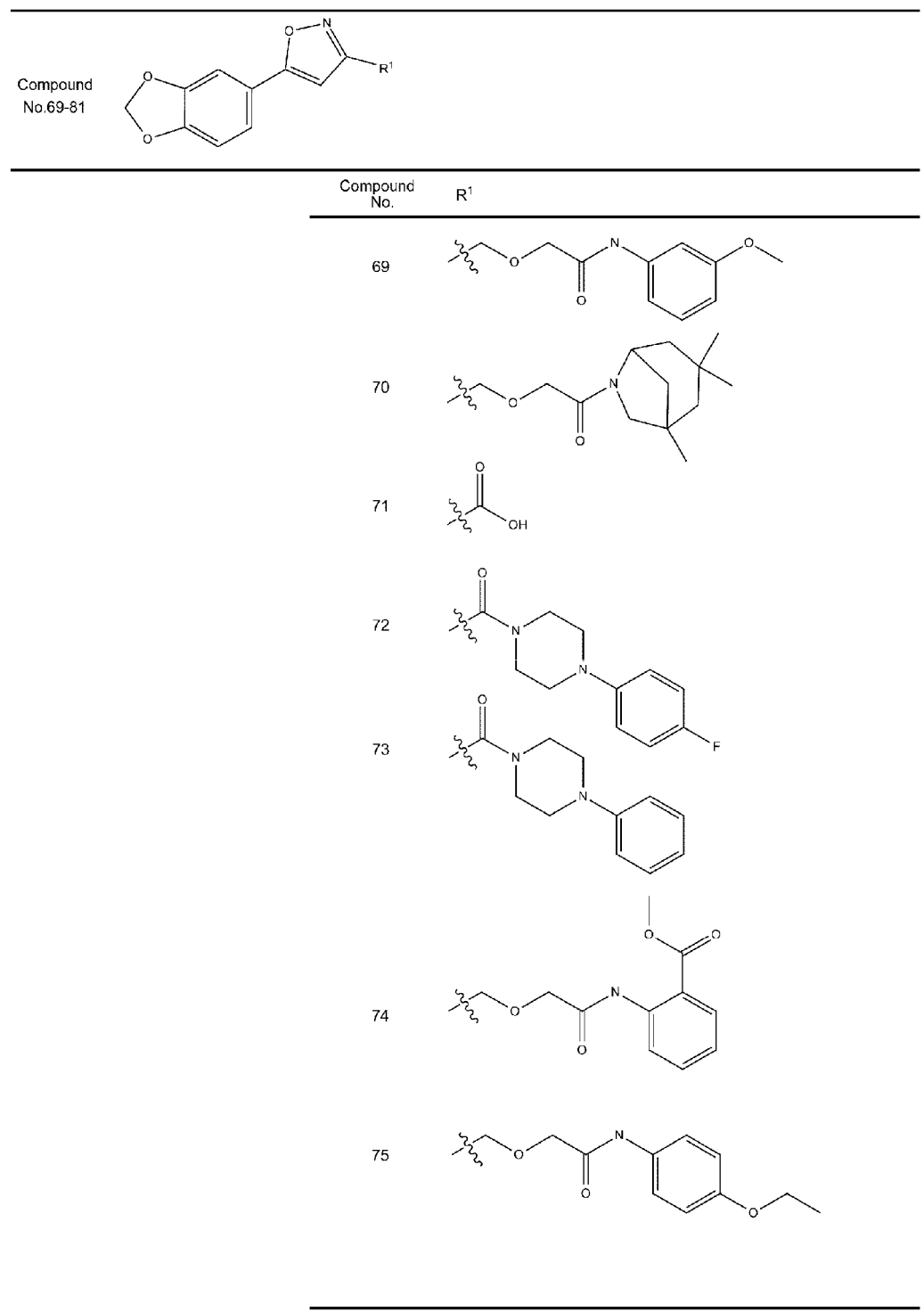
Figures 6, 7, 8, 9, 10, 11:
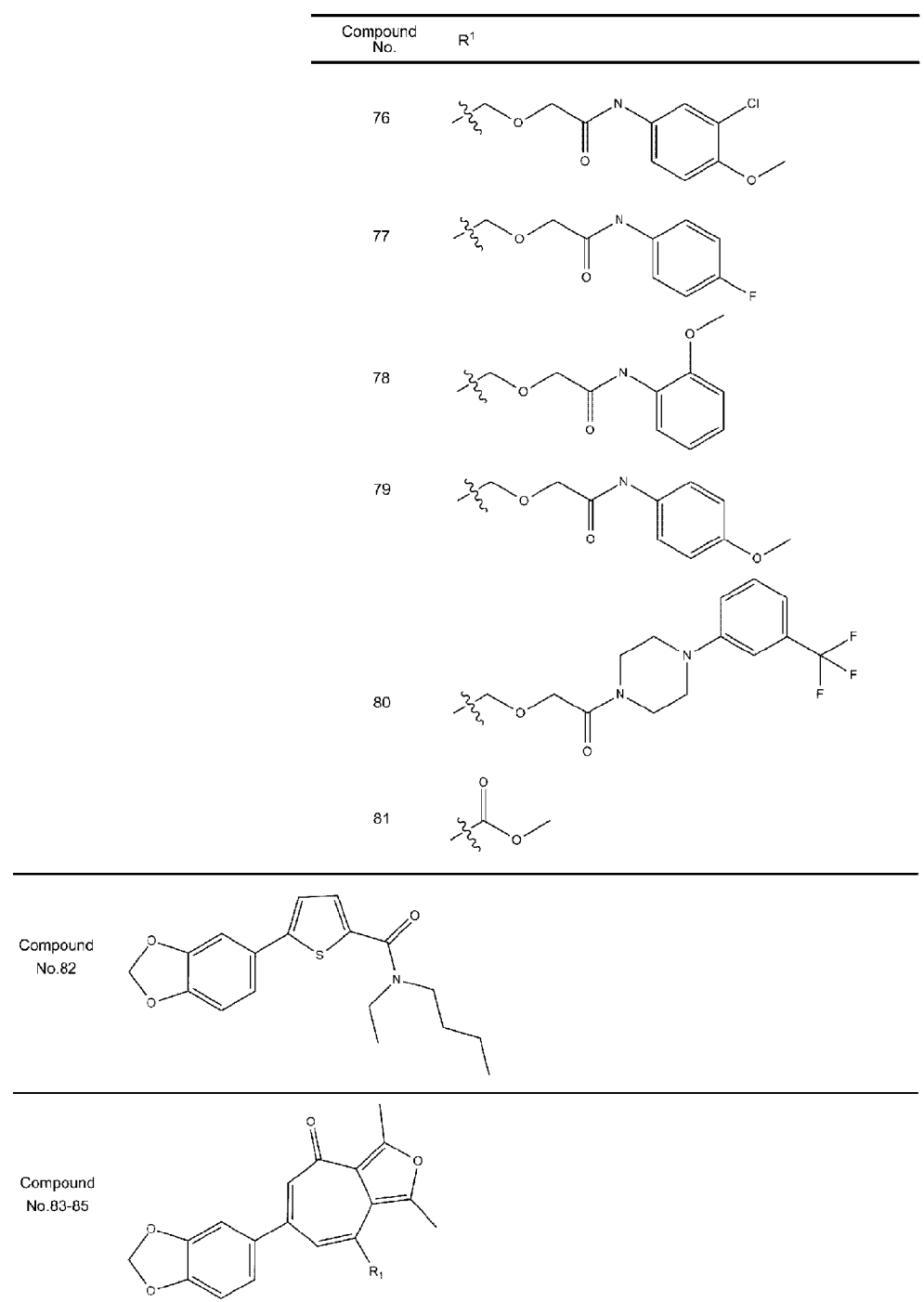
Figures 6, 7, 8, 9, 10, 11, 12, 13:
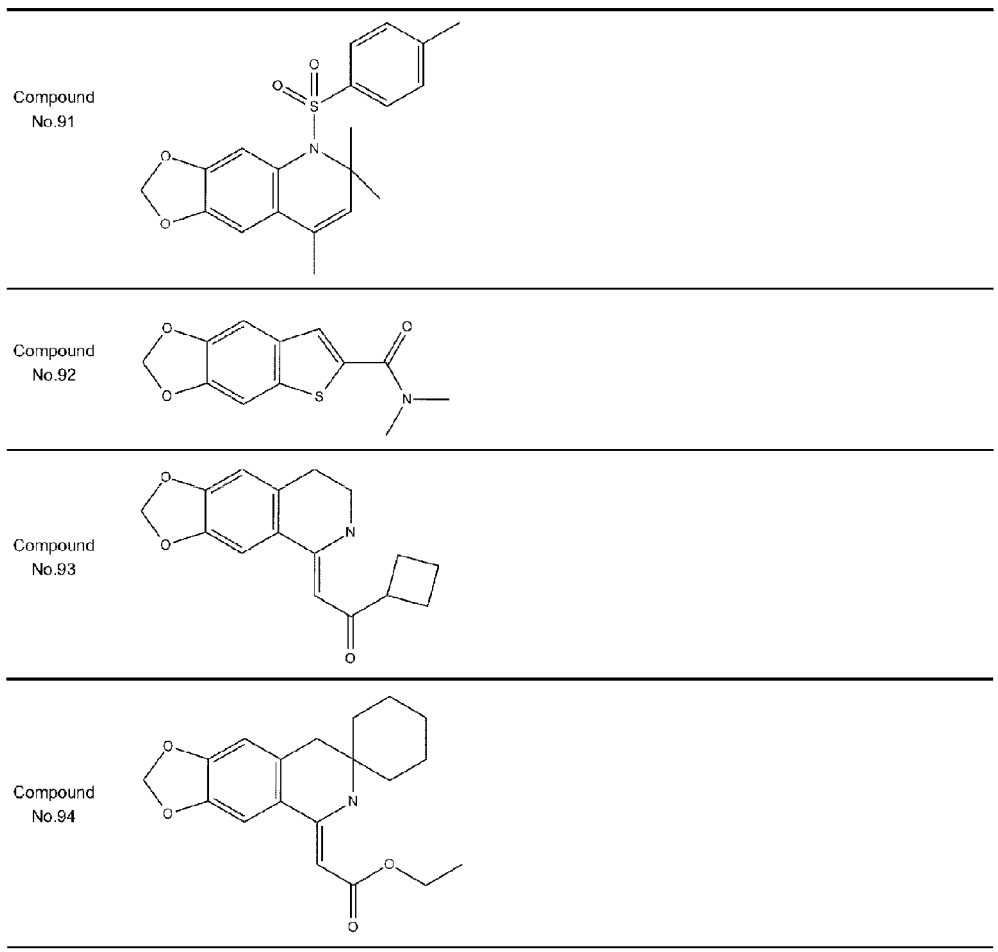

Details of the 94 compounds are as follows (FIG. 6). Compound Nos. 1 to 44 are compounds in which various substituents are bonded to the carbon at the 3-position of 1-propenyl of isosafrole (FIGS. 6-1 to 6-6). Specifically, the following compounds are included. Compounds (Nos. 1-9 and 11-13) in which a carbonyl group is formed at the 3-position of the propenyl group ($R^e$ and $R^f$ in formula III are =O) and a substituent containing an aromatic ring is also bound at the 3-position ($R^g$ in formula III contains a substituted or unsubstituted aryl or heteroaryl group). Compound (No. 14) in which, at the 3-position of the propenyl group, an oxime group is formed ($R^e$ and $R^f$ in formula III are =$NR^{21}$) and also an aromatic ring is bound. Compounds (Nos. 15-17) in which an ester bond is formed at the 3-position of the propenyl group ($R^g$ in formula III is —O—$X^{32}$—$R^{32}$). Compounds (Nos. 18-39) in which an amide bond is formed at the 3-position of the propenyl group ($R^g$ in formula III is —N(—$X^{33}$—$R^{33}$) (—$X^{34}$—$R^{34}$)). Compounds (Nos. 40-43) in which not only a carbonyl group is formed at the 3-position of the propenyl group, but also various substituents are bound to the 1-position and the 2-position ($R^c$ and $R^d$ in formula III are other than hydrogen atoms). Compound (No. 44) having a uracil structure bound through the carbon at the 3-position of the propenyl group ($R^e$ and $R^f$ together represent =$CR^{21}R^{22}$ and $R^e.R^f$ and $R^g$ together form a ring structure). Compound No. 10 is a compound in which the hydroxyl group in stiripentol is substituted with a carbonyl group and one of the carbons of the tertiary butyl group is substituted with a hydroxy group. In addition, some of Compound Nos. 1-44 have various substituents bound to positions other than the 5-position of the benzene ring of 1,3-benzodioxole of isosafrole ($R^a$, $R^b$ or $R^h$ in formula III is other than a hydrogen atom).

Next, Compound Nos. 45-68 are compounds in which a C—C bond between the 2- and 3-position of the 1-propenyl group of isosafrole forms part of the ring structure ($R^d$ and $R^g$ in formula III together form a ring structure) (FIGS. 6-6 to 6-9). Specifically, the following compounds are included. Compounds (Nos. 45-58) which are bonded to a 5-membered ring through a C—C bond between the 2- and 3-position of the propenyl group. The constituent elements of the five-membered ring include not only carbon, but also heterocyclic rings composed of nitrogen, oxygen and sulfur are included. For all of Compound Nos. 45-58, a carbonyl group is formed at the 3-position of the propenyl group. Compounds (Nos. 59 and 60) which are bonded to a quinuclidine structure through a C—C bond between the 2- and 3-position of the propenyl group. Compounds (Nos. 61-68) which are bound to a condensed ring comprising a five-membered ring and a six-membered ring via C—C bond between the 2- and 3-position of the propenyl group. For all of Compound Nos. 61-68, a carbonyl group is formed at the 3-position of the propenyl group. In addition, some of Compound Nos. 45-68 have various substituents bound to positions other than the 5-position of the benzene ring of 1,3-benzodioxole of isosafrole.

Further, Compound Nos. 69-94 are compounds in which the C=C—C bond at positions 1 to 3 of the 1-propenyl group of isosafrole forms part of a ring structure ($R^c$ and $R^e.R^f$ or $R^c$ and $R^g$ in formula III together form a ring structure) (FIGS. 6-10 to 6-12; Nos. 69-87), or compounds in which all or part of the 1-propenyl group of isosafrole form a tricyclic compound ($R^b$ and $R^c$, $R^b$ and $R^d$ or $R^b$ and $R^g$ in formula III together form a ring structure) (FIG. 6-12 to 6-13; Nos. 88-94). Specifically, the following compounds are included. Compounds (Nos. 69-81) in which the C=C—C bond at positions 1 to 3 of the propenyl group form part of a isoxazole structure, and Compound (No. 82) which are a part of the thiophene structure. Compounds (Nos. 83-87) in which a C=C—C bond at positions 1 to 3 of the propenyl group form part of a bicyclic compound. Tricyclic compounds (Nos. 88-91) in which a nitrogen is bound to the 3-position of the propenyl group and the resultant is bound to the 6-position of 1,3-benzodioxole. Tricyclic compound (No. 92) in which a sulfur is bound to the 2-position of the propenyl group and the resultant is bound to the 6-position of 1,3-benzodioxole. Tricyclic compounds (Nos. 93 and 94) in which a nitrogen is bound to the 1-position of the propenyl group and the resultant is bound to the 6-position of 1,3-benzodioxole via a carbon chain. In the above 94 compounds, inhibitory activities on lactate dehydrogenase were observed (FIG. 7).

From the above, it was revealed that isosafrole has "lactate dehydrogenase inhibitory action" and is an "anti-epileptic drug" effective for refractory epilepsy for which stiripentol is not effective. It was also revealed that many of the compounds having isosafrole as a scaffold have an inhibitory action on lactate dehydrogenase.

The invention claimed is:

1. A drug comprising a compound represented by formula (III) as an active ingredient:

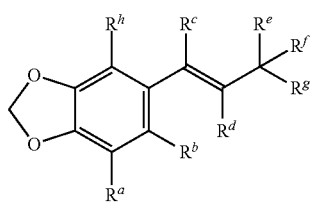
(III)

wherein
$R^a$ represents a hydrogen atom, a halogen atom or alkoxy optionally substituted with halogen atoms;
$R^b$ represents a hydrogen atom, a halogen atom, or alkoxy optionally substituted with halogen atoms or nitro;
$R^c$ represents a hydrogen atom or carboxyl;
$R^d$ represents a hydrogen atom or $-X^{11}-R^{11}$;
$X^{11}$ represents alkylene, —NH—CO—, —CH$_2$—NR$^{12}$—CO— or —S—;
$R^{11}$ represents aryl optionally having substituents, carboxyl, alkyl optionally substituted with halogen atoms, or hydroxyalkyl;
$R^{12}$ represents hydroxyalkyl;
for $R^e$, $R^f$ and $R^g$:
(a) $R^e$ and $R^f$ together represent =O, and $R^g$ represents any of the following structures:

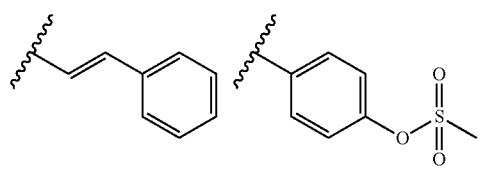

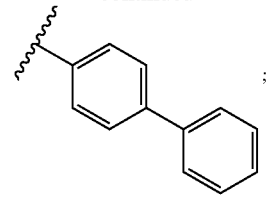
;

or
(b) $R^e$ and $R^f$ together represent =O, and $R^g$ represents —NHR$^{34}$, where $R^{34}$ represents any of the following structures:

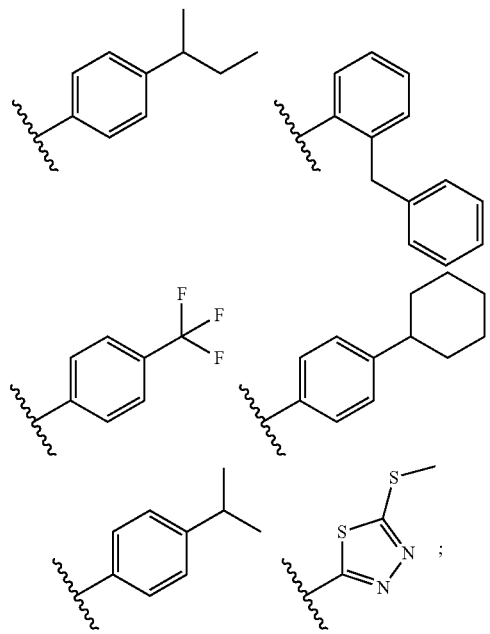
;

and
$R^h$ represents a hydrogen atom or a halogen atom.

2. A method for inhibiting a lactate dehydrogenase comprising contacting the lactate dehydrogenase with a compound represented by formula (III):

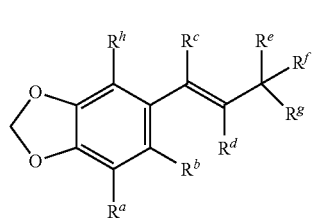
(III)

wherein
$R^a$ represents a hydrogen atom, a halogen atom or alkoxy optionally substituted with halogen atoms;
$R^b$ represents a hydrogen atom, a halogen atom, or alkoxy optionally substituted with halogen atoms or nitro;
$R^c$ represents a hydrogen atom or carboxyl;
$R^d$ represents a hydrogen atom or $-X^{11}-R^{11}$;
$X^{11}$ represents alkylene, —NH—CO—, —CH$_2$—NR$^{12}$—CO— or —S—;

R[11] represents aryl optionally having substituents, carboxyl, alkyl optionally substituted with halogen atoms, or hydroxyalkyl;

R[12] represents hydroxyalkyl;

for $R^e$, $R^f$ and $R^g$:

(a) $R^e$ and $R^f$ together represent =O, and $R^g$ represents any of the following structures:

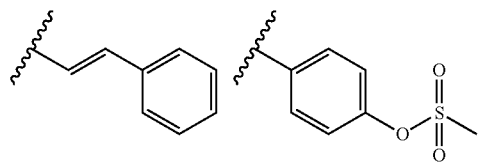

or (b) $R^e$ and $R^f$ together represent =O, and $R^g$ represents —NHR[34], where R[34] represents any of the following structures:

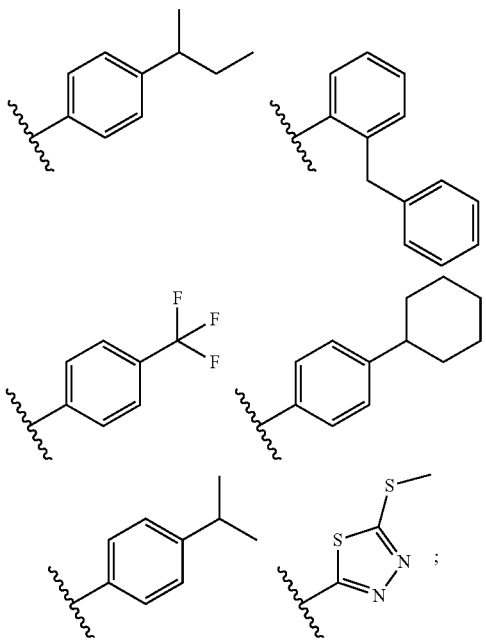

and $R^h$ represents a hydrogen atom or a halogen atom.

3. A method for treating epilepsy comprising administrating an effective amount of a compound represented by formula (III) to a subject of epilepsy:

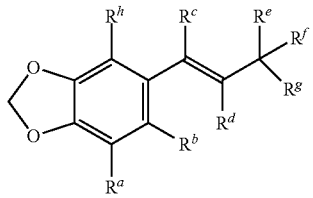

wherein $R^a$ represents a hydrogen atom, a halogen atom or alkoxy optionally substituted with halogen atoms;

$R^b$ represents a hydrogen atom, a halogen atom, or alkoxy optionally substituted with halogen atoms or nitro;

$R^c$ represents a hydrogen atom or carboxyl;

$R^d$ represents a hydrogen atom or —X[11]—R[11];

X[11] represents alkylene, —NH—CO—, —CH$_2$—NR[12]—CO— or —S—;

R[11] represents aryl optionally having substituents, carboxyl, alkyl optionally substituted with halogen atoms, or hydroxyalkyl;

R[12] represents hydroxyalkyl;

for $R^e$, $R^f$ and $R^g$:

(a) $R^e$ and $R^f$ together represent =O, and $R^g$ represents any of the following structures:

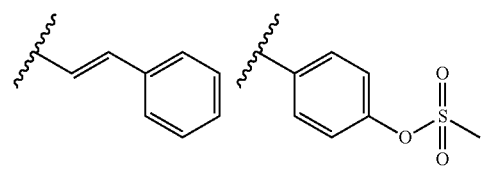

or (b) $R^e$ and $R^f$ together represent =O, and $R^g$ represents —NHR[34], where R[34] represents any of the following structures:

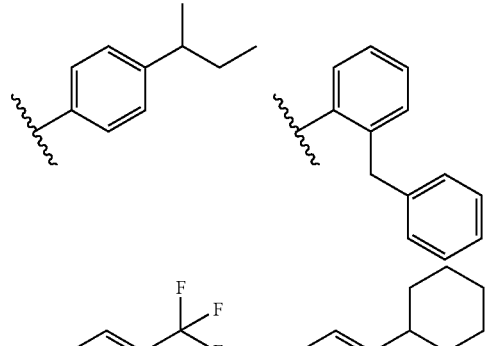

-continued
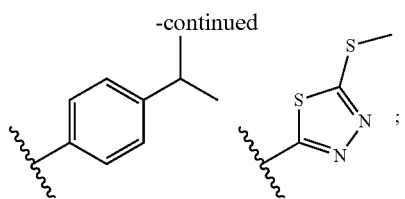
and
$R^h$ represents a hydrogen atom or a halogen atom.
* * * * *